US006855500B2

(12) United States Patent
Wolfe et al.

(10) Patent No.: US 6,855,500 B2
(45) Date of Patent: Feb. 15, 2005

(54) FLUORESCENCE-BASED GENOTYPING

(75) Inventors: Jia Liu Wolfe, Winchester, MA (US); Tomohiko Kawate, Cambridge, MA (US); Charles R. Allerson, Carlsbad, CA (US); Vincent P. Stanton, Jr., Belmont, MA (US)

(73) Assignee: Sequenom, Inc., San Diego, CA (US)

( * ) Notice: Subject to any disclaimer, the term of this patent is extended or adjusted under 35 U.S.C. 154(b) by 392 days.

(21) Appl. No.: 10/107,748

(22) Filed: Mar. 26, 2002

(65) Prior Publication Data

US 2003/0165880 A1 Sep. 4, 2003

Related U.S. Application Data

(63) Continuation-in-part of application No. 09/394,467, filed on Sep. 10, 1999, now Pat. No. 6,566,059.
(60) Provisional application No. 60/102,724, filed on Oct. 1, 1998.

(51) Int. Cl.[7] .............................. C12Q 1/68; C12P 19/34
(52) U.S. Cl. .......................................... 435/6; 435/91.2
(58) Field of Search ................................... 435/6, 91.2

(56) References Cited

U.S. PATENT DOCUMENTS

| 4,701,419 A | 10/1987 | Morris ........................ 436/89 |
| 4,879,214 A | 11/1989 | Kornher et al. ............... 435/91 |
| 5,003,059 A | 3/1991 | Brennan ...................... 536/27 |
| 5,064,754 A | 11/1991 | Mills ............................ 435/6 |
| 5,174,962 A | 12/1992 | Brennan ...................... 422/78 |
| 5,187,085 A | 2/1993 | Lee ............................. 435/91 |
| 5,221,518 A | 6/1993 | Mills ............................ 422/62 |
| 5,332,666 A | 7/1994 | Prober et al. ................ 435/91.5 |
| 5,424,184 A | 6/1995 | Santamaria et al. ............ 435/6 |
| 5,547,835 A | 8/1996 | Köster .......................... 435/6 |
| 5,552,278 A | 9/1996 | Brenner ........................ 435/6 |
| 5,580,733 A | 12/1996 | Levis et al. .................... 435/6 |
| 5,605,798 A | 2/1997 | Köster .......................... 435/6 |
| 5,622,824 A | 4/1997 | Köster .......................... 435/6 |
| 5,691,141 A | 11/1997 | Köster .......................... 435/6 |
| 5,700,642 A | 12/1997 | Monforte et al. ............... 435/6 |
| 5,830,655 A | 11/1998 | Monforte et al. ............... 435/6 |
| 5,869,242 A | 2/1999 | Kamb ........................... 435/6 |
| 5,939,292 A | 8/1999 | Gelfand et al. ............... 435/91.2 |
| 6,500,650 B1 * | 12/2002 | Stanton et al. ............... 435/91.1 |
| 6,610,492 B1 * | 8/2003 | Stanton et al. ................. 435/6 |

FOREIGN PATENT DOCUMENTS

WO    WO98/00433    1/1998

OTHER PUBLICATIONS

Andersson, B. et al., "Simultaneous shotgun sequencing of multiple cDNA clones," *DNA Sequence*, 1997, 7:63–70.

Astatke, M., et al, "Deoxynucleoside triphosphate and pyrophosphate binding sites in the catalytically competent ternary complex for the pholymerase reaction catalyzed by DNA polymerase I (Klenow fragment)," *J. Biol. Chem.*, 1995, 270: 1945–54.

Astatke, M., et al. "How *E. coli* DNA polymerase I (Klenow fragment) distinguishes between Deoxy–and Dideoxynucleotides," *J. Mol. Biol.*, 1998, 278:147–165.

Astatke, M., et al., "A single side chain prevents *Escherichia coli* DNA polymerase I (Klenow fragment) from incorporating ribonucleotides," *Proc. Natl. Acad. Sci. USA*, 1998, 95:3402–3407.

(List continued on next page.)

Primary Examiner—Kenneth R. Horlick
(74) *Attorney, Agent, or Firm*—Bernard F. Rose, Esq.; Bingham McCutchen LLP

(57) ABSTRACT

The present invention relates to a method for genotyping a diploid organism to detect single nucleotide polymorphisms (SNPs) using modified nucleotides or nucleotide residues substituted with fluorescent groups.

26 Claims, 9 Drawing Sheets

OTHER PUBLICATIONS

Barnes, W.M., "DNA Sequencing by Partial Ribosubstitution," *J. Mol.Bio.*, 1978, 119:83–99.

Barnes, W.M., "PCR amplification of up to 35–kb DNA with high fidelity and high yield from λ bacteriophage templates," *Proc. Natl. Acad. Sci.* USA, 1994, 91:2216–2220.

Beavis, R., et al "Matrix–assisted laser desorption/ionization mass spectrometry of biopolymers," *Anal. Biochem.*, 1991, 63: 1193–1203.

Chen, C. N., et al, "Ordered shotgun sequencing of a 135 kb Xq25 YAC containing ANT2 and four possible genes, including three confirmed by EST matches," *Nucleic Acids Research*, 1996, 24:4034–4041.

Daugherty P.S., et al., "Antibody affinity maturation using bacterial surface display," *Protein Eng* 1998, 11:825–32.

Delarue, M., et al., "An attempt to unify the structure of polymerases," *Protein Eng,* 1990, 3:461–467.

Fichant, G. A. and Quentin, Y., "A frameshift error detection algorithm for DNA sequencing projects," *Nucleic Acid Research,* 23:2900–2908, 1995.

Fu, D. J., et al., "Sequencing exons 5 to 8 of the p53 gene by MALDI–TOF mass spectrometry," *Nature Biotechnology*, 1998, 16:381–384.

Giese, B., et al, "The chemistry of single–stranded 4'–DNA radicals: influence of the radical precursor o anaerobic and aerobic strand cleavage," *Chemistry & Biology*, 1995, 2 No. 6, 367–375.

Giese, B., et al, "The mechanism of anaerobic, Radical–Induced DNA strand scission," *Angew. Chem. Int. Ed. Engl.* 1993, 32:1742–43.

Gish, G., et al "DNA and RNA Sequence Determination Based on Phosphorothioate Chemistry," *Reports*, 1988 1520–1522.

Gupta and Kool, "A self–cleaving DNA nucleoside," *Chem. Commun.* 1997, pp 1425–26.

Harayama, S., "Artificial evolution by DNA shuffling,"0 *Trends Biotechnol.*, 1998, 16:76–82.

Hentosh, P. et al, "Polymerase chain reaction amplification of single–stranded DNA containing a base analog, 2–Chloroadenine,". *Anal. Biochem.*, 1992, 201: 277–281.

Huang, Y., "Determinants of Ribose Specifity in RNA Polymerization: Effects of $Mn^{2+}$ and Deoxynucleotide Monophosphate Incorporation into Transcripts," *Biochemistry*, 1997, 36:13718–13728.

Joyce, C. M., "Choose the right sugar: How polymerase select a nucleotide substrate," *Proc. Natl. Acad. Sci.* USA, 1997, 94:1619–1622.

Kaczorowski, T., et al., "Assembly of 18–nucleotide primers by ligation of three hexamers: secuqhcing of large genomes by primer walking," *Anal. Biochem.*1994, 221:127–135.

Khurshid, F., et al, "Error analysis in manual and automated DNA sequencing," *Analytical Biochemistry*, 208:138–143, 1993.

Kirpekar, F., et al, "Matrix–assisted laser desorption–ionization mass spectrometry of enzymatically synthesized RNA up to 150 kDa," *Nucleic Acids Research*, 1994, 22: No. 19 3866–3870.

Kistensen, T., et al., "An estimate of the sequencing error frequency in the DNA sequence databases," *DNA Sequencing*, 2:343–346, 1992.

Landegren, U. et al., Reading Bits of Genetic Information: Methods for Single–nucleotide Polymorphism Analysis, *Genome Research* 1998, 88:769–76.

Liu, D., et al., "Bi–stranded, multisite replication of a base pair between difluorotoluene and Adenine: confirmation by 'inverse' sequencing," *Chem. Biol.*, 4:919–929, 1997.

Lodhi, M. A., et al., "High–quality automated DNA sequencing primed with hexamer strings," *Genome Research*, 1996, 6:10–18.

Martin–Gallardo, et al., "Automated DNA sequencing and analysis of 106 kilobases from human chromosome 19q13.3," *Nature Genetics*, 1992 1:34–39.

Marx, A., et al., "Synthesis of 4–C–Acylated Thymidines," *Helv. Chim. Acta*. 1966, 79:1980–94.

Maxam and Gilbert, "A new method for sequencing DNA" *Proc. Nat. Acad. Sci.* USA, 74, 560–564 1977.

Moran, S., et al., "A thymidine triphosphate shape analog lacking Watson–Crick pariing ability is replicated with high sequence selectivity," *Proc. Natl. Acad. Sci.* USA, 94:10506–10511, 1997.

Nakamaye, K. et al, "Direct sequencing of polymerase chain reaction amplified DNA fragments through the incorporation of deoxynucleoside α–thiotriphosphates," *Nucleic Acid Research*, 1988, 16:9947–9959.

Nelson, R.W., et al, "Volatilization of High Molecular Weight DNA by Pulsed Laser Ablation of Frozen Aqueous Solutions," *Science* 1989, vol. 246, 1585–1587.

Nickerson, D.A., "DNA sequence diversity in a 9.7–kb region of the human lipoprotein ilipase gene," *Nature Genetics*, 1998, 223–240.

Nordhoff, E. et al., "Comparison of IR–and UV–matrix–assisted laser desorption/ionization mass spectrometry of oligodeoxynucleotides," *Nucleic Acids Research*, 1994, 22: No. 13, 2460–2465.

Nordhoff, E. et al, "Ion stability of nucleic acids in infrared matrix–assisted laser desorption/ionization mass spectrometry," *Nucleic Acids Research*, 1993, 21:No. 15 3347–3357.

Olsen, D.B. et al, "[8] Direct sequencing of polymerase chain reaction products," *Methods of Enzymology*, vol. 218 pp 79–92, 1993.

Ono, T., et al., "2'–Floro modified nucleic acids: polymerase–directed synthesis, properties and stability to analysis by matrix–assisted laser desorption/ionization mass spectrometry," *Nucleic Acids Research*, 1997, 25: 4581–4588.

Pedersen et al., "A method for directing evolution and functional cloning of enzymes," *Proc. Natl. Acad. Sci.* USA, 1998, 95:10523–8.

Pieles, U, et al., "Matrix–assisted laser desorption ionization time–of–flight mass spectrometry: a powerful tool for the mass and sequence analysis of natural and modified oligonucleotides," *Nucleic Acids Research*, 1993, 21:No. 14 3191–3196.

Polesky et al., "Identification of residues critical for the polymerase activity of the Klenow fragment of DNA polymerase I from *Escherichia coli*", *J. Biol. Chem.*, 1990, 265:14579–91.

Pomerantz, S.C., et al., "Determiniation of oligonucletodie composition from Mass spectrometrically measured molecular weight," *J. Am. Soc. Mass Spectrom.*, 1993, 4: 204–209.

Prober, et al, "A System for Rapid DNA Sequencing with Fluorescent Chain–Terminating Dideoxynucleotides," *Science* 1987, vol. 238, 336–341.

Sanger, et al., "DNA sequencing with chain–terminating inhibitors," *Proc. Nat. Acad. Sci.* USA, 74, 5463–5467 1977.

Schneider, K. and Chait, B.T., "Increased stability of nucleic acids containing 7–deaza–quanosine and 7–deaza–adenosine may enable rapid DNA sequencing by matrix–assisted laser desorption mass spectrometry," *Nucleic Acids Research*, 1995, 23:1570–1575.

Siebenlist, et al., "Contacts between *Escherichia coli* RNA polymerase and an early promoter of phae T7," *Proc. Natl. Acad. Sci.* USA, 1980, 77:122.

Siuzdak, G. "The emergence of mass spectrometry in biochemical research," *Proc. Natl. Acad. Sci.*, 1994, 91:11290–11297.

Sousa, et al, "A mutant T7 RNA polymerase as a DNA polymerase," *EMBO Journal* vol. 14 No. 18, pp. 4609–4621, 1995.

Stemmer, W. P. C., "Rapid evolution of a protein in vitro by DNA shuffling," *Nature*, 1994, 370:389–391.

Tabor, S., et al., "DNA sequence analysis with a modified bacteriophage T7 DNA polymerase," *Proc. Natl. Acad. Sci.* USA, 1987, 84:4767–4771.

Venter, J. C., et al., "Shotgun sequencing of the human genome," *Science*, 1998, 280:1540–1542.

Verdine, et al, "Immobilized Metal Affinity Chromatography of DNA," *Dept. of Chemistry, Harvard University*, May 29, 1996.

Verdine, et al., "Template–Directed Interference Footprinting of Cytosine Contacts in s Protein–DNA Complex: Potent Interference by 5–Aza–2'–deoxycytidine," *Biochemistry*, 1992, 31:11265–11273.

Verdine, et al., "Template–Directed Interference Footprinting of Protein–Adenine Contacts," *JACS* , 1996, 118:6116–6120.

Verdine, et al., "Template–Directed Interference Footprinting of Protein–Guanine Contacts in DNA;" *JACS*, 1991, 113:5104–5106.

Verdine, et al., "Template–Directed Interference Footprinting of Protein–Thymine COntacts," *JACS*, 1993, 115: No. 1 373–374.

Voss, H., et al., "Automated low–redundancy large–scale DNA sequencing by primer walking," *Biotechniques.* 1993, 15:714–721.

Wang, B. H., et al "Matrix–assisted laser desorption/ionization time–of–flight mass spectrometry of chemically modified oligonucleotides," *Analytical Chemical*, 1994, 66: 1918–1924.

Wang, B. H., et al, Sequencing of modified oligonucleotides using in–source fragmentation and delayed pulsd ion extraction matrix–assisted laser desorption ionixation time–of–flight mass spectrometry, *Internat'l J. of Mass Spec. and ion Process*, 1997, 169/170:331–350.

Weber, J. L. "Human whole–genome shotgun sequencing," *Genome Research*, 1997, 7:401–409.

Williams, E. R., "Tandem FTMS of Large Biomolecules," *Anal. Chem.*, 1998, 70:179A–185A.

Wu, K., et al., "Time–of–flight mass spectrometry of underivatized single–stranded DNA oligomers by matrix–assisted laser desorption," *Anal. Chem.*, 1994 66, 1637–1645.

* cited by examiner

STEP 1

STEP 2

STEP 3

FIGURE 7A

Primer 1
5' - GAAACTGGACAGCACAGACTTCACCAGCACCATCAAGCTGCTGAATGA - 3' [SEQ. ID. NO. 3]

3' - CTTTGACCTGTCGTGTCTGAAGTGGTCGTGGTAGTTCGACGACTTACT - 5' [SEQ. ID. NO. 4]
Primer 2

Primer 1
5' - GAAACTGGACAGCACAGACTTCACCAGCACCATCAAGCTGCTGAATGA - 3' [SEQ. ID. NO. 5]

3' - CTTTGACCTGTCGTGTCTGAAGTGGTCGTGGTAGTTCGACGACTTACT - 5' [SEQ. ID. NO. 6]
Primer 2

Primer 1
5' - GAAACTGGACAGCACAGACTTCACCAGCACCATCAAGCTGCTGAATGAAAATTCATATGTCCCTCGTGAGGCTGGATCTC - 3'
[SEQ. ID. 7]

3' - CTTTGACCTGTCGTGTCTGAAGTGGTCGTGGTAGTTCGACGACTTACTTTTAAGTATACAGGGAGCACTCCGACCTAGAG - 5'
[SEQ. ID. 8]
Primer 2

Primer 1
5' - GAAACTGGACAGCACAGACTTCACCAGCACCATCAAGCTGCTGAATGAAAATTCATATGTCCCTCGTGAGGCTGGATCTCA - 3'
[SEQ. ID. 9]

3' - CTTTGACCTGTCGTGTCTGAAGTGGTCGTGGTAGTTCGACGACTTACTTTTAAGTATACAGGGAGCACTCCGACCTAGAGTT - 5'
[SEQ. ID. 10]
Primer 2

FIGURE 7B from (rG/NO₂dA)TP: 25nt+ 5'-GAAACTGGACAGCACAGACTTCACC [SEQ. ID. NO. 11]

21nt 3'-GTGGTAGTTCGACGACTTACT-5' [SEQ. ID.NO.12]

from rGTP: 27nt 5'-GAAACTGGACAGCACAGACTTCACCAG [SEQ. ID. NO. 13]

22nt 3'-GGGAGCACTCCGACCTAGAGTT-5' [SEQ. ID. NO. 14]

from NO₂ATP: 25nt+ 5'-GAAACTGGACAGCACAGACTTCACC [SEQ. ID. NO. 15]

22nt+ 3'-GGGAGCACTCCGACCTAGAGTT-5' [SEQ. ID. NO. 16]

+ indicates a TCEP adduct

US 6,855,500 B2

SEQUENCE LISTING

<160> NUMBER OF SEQ ID NOS: 16

<210> SEQ ID NO 1
<211> LENGTH: 192
<212> TYPE: DNA
<213> ORGANISM: Artificial
<220> FEATURE:
<223> OTHER INFORMATION: Artificial test sequence used to demonstrate invention

<400> SEQUENCE: 1
gcctcctgct catgatccta cauccggaug ugcagcguga gcccaucugg gaaacagugc       60
aggggccgag ggaggaaggg uacaggcggg ggcccacgga ggacgaguac uaggauguag      120

```
gccuacacgu cgcacucggg uagacccuuu gucacguccc cggcucccuc cuucccaugu    180
ccgcccccgg gu                                                        192
```

<210> SEQ ID NO 2
<211> LENGTH: 190
<212> TYPE: DNA
<213> ORGANISM: Artificial
<220> FEATURE:
<223> OTHER INFORMATION: Artificial sequence used to demonstrate
      invention.

<400> SEQUENCE: 2

```
ugaacuuugc ugggacaccc ggggcuccaa gcacaggcuu gaccaggauc cuguaagccu     60
gaccuccucc aacauaggag gcaagaagga gugucacuug aaacgacccu gugggccccg    120
accuucgugu ccgaacuggu ccuaggacau ucggacugga ggaguugua tcctccgttc    180 ttcctcacag                                                           190
```

<210> SEQ ID NO 3
<211> LENGTH: 48
<212> TYPE: DNA
<213> ORGANISM: Artificial
<220> FEATURE:
<223> OTHER INFORMATION: Transferrin receptor sequence used to
      demonstrate invention.

<400> SEQUENCE: 3

```
gaaactggac agcacagact tcaccagcac catcaagctg ctgaatga                 48
```

<210> SEQ ID NO 4
<211> LENGTH: 48
<212> TYPE: DNA
<213> ORGANISM: Artificial
<220> FEATURE:
<223> OTHER INFORMATION: Transferin receptor sequence used to
      demonstrate invention.

<400> SEQUENCE: 4

```
ctttgacctg tcgtgtctga agtggtcgtg gtagttcgac gacttact                 48
```

<210> SEQ ID NO 5
<211> LENGTH: 48
<212> TYPE: DNA
<213> ORGANISM: Artificial
<220> FEATURE:
<223> OTHER INFORMATION: Transferrin receptor sequence used to
      demonstrate invention.

<400> SEQUENCE: 5

```
gaaactggac agcacagact tcaccagcac catcaagctg ctgaatga                 48
```

<210> SEQ ID NO 6
<211> LENGTH: 48
<212> TYPE: DNA
<213> ORGANISM: Artificial
<220> FEATURE:
<223> OTHER INFORMATION: Transferin receptor sequence used to
      demonstrate invention,

<400> SEQUENCE: 6

```
ctttgacctg tcgtgtctga agtggtcgtg gtagttcgac gacttact                 48
```

<210> SEQ ID NO 7
<211> LENGTH: 80
<212> TYPE: DNA
<213> ORGANISM: Artificial
<220> FEATURE:
<223> OTHER INFORMATION: Transferrin receptor sequence used to
      demonstrate invention.

<400> SEQUENCE: 7
gaaactggac agcacagact tcaccagcac catcaagctg ctgaatgaaa attcatatgt    60
ccctcgtgag gctggatctc                                               80

<210> SEQ ID NO 8
<211> LENGTH: 80
<212> TYPE: DNA
<213> ORGANISM: Artificial
<220> FEATURE:
<223> OTHER INFORMATION: Treanferrin receptor sequence used to
      demonstrate invention.

<400> SEQUENCE: 8
ctttgacctg tcgtgtctga agtggtcgtg gtagttcgac gacttacttt taagtataca    60
gggagcactc cgacctagag                                               80

<210> SEQ ID NO 9
<211> LENGTH: 81
<212> TYPE: DNA
<213> ORGANISM: Artificial
<220> FEATURE:
<223> OTHER INFORMATION: ransferrin receptor sequence used to
      demonstrate invention.

<400> SEQUENCE: 9
gaaactggac agcacagact tcaccagcac catcaagctg ctgaatgaaa attcatatgt    60
ccctcgtgag gctggatctc a                                             81

<210> SEQ ID NO 10
<211> LENGTH: 82
<212> TYPE: DNA
<213> ORGANISM: Artificial
<220> FEATURE:
<223> OTHER INFORMATION: Transferin receptor sequence used to
      demonstrate invention.

<400> SEQUENCE: 10
ctttgacctg tcgtgtctga agtggtcgtg gtagttcgac gacttacttt taagtataca    60
gggagcactc cgacctagag tt                                            82

<210> SEQ ID NO 11
<211> LENGTH: 25
<212> TYPE: DNA
<213> ORGANISM: Artificial
<220> FEATURE:
<223> OTHER INFORMATION: Expected fragments from transferrin receptor
      sequence after cleavage.

<400> SEQUENCE: 11
gaaactggac agcacagact tcacc                                         25

<210> SEQ ID NO 12
<211> LENGTH: 21
<212> TYPE: DNA
<213> ORGANISM: Artificial

```
<220> FEATURE:
<223> OTHER INFORMATION: Expected fragment of transferrin receptor
      after cleavage.

<400> SEQUENCE: 12
gtggtagttc gacgacttac t                                             21

<210> SEQ ID NO 13
<211> LENGTH: 27
<212> TYPE: DNA
<213> ORGANISM: Artificial
<220> FEATURE:
<223> OTHER INFORMATION: Expected fragment of transferrin receptor
      cleavage.

<400> SEQUENCE: 13
gaaactggac agcacagact tcaccag                                       27

<210> SEQ ID NO 14
<211> LENGTH: 22
<212> TYPE: DNA
<213> ORGANISM: Artificial
<220> FEATURE:
<223> OTHER INFORMATION: Expected fragment of transferrin receptor
      cleavage.

<400> SEQUENCE: 14
gggagcactc cgacctagag tt                                            22

<210> SEQ ID NO 15
<211> LENGTH: 25
<212> TYPE: DNA
<213> ORGANISM: Artificial
<220> FEATURE:
<223> OTHER INFORMATION: Expected fragment from transferrin receptor
      cleavage.

<400> SEQUENCE: 15
gaaactggac agcacagact tcacc                                         25

<210> SEQ ID NO 16
<211> LENGTH: 22
<212> TYPE: DNA
<213> ORGANISM: Artificial
<220> FEATURE:
<223> OTHER INFORMATION: Expected fragment from transferrin receptor
      cleavage.

<400> SEQUENCE: 16
gggagcactc cgacctagag tt                                            22
```

FLUORESCENCE-BASED GENOTYPING

RELATED APPLICATIONS

This application is a continuation-in-part of U.S. Ser. No. 09/394,467 to Stanton, Wolfe, and Verdine, filed Sep. 10, 1999, entitled "A METHOD FOR ANALYZING POLYNUCLEOTIDES", U.S. Pat. No. 6,566,059. Ser. No. 09/394,467 in turn claims the benefit of U.S. Provisional Patent Application, serial No. 60/102,724, filed Oct. 1, 1998, also entitled "A METHOD FOR ANALYZING POLYNUCLEOTIDES." Both are incorporated by reference in their entireties, including drawings and tables, as if fully set forth herein.

FIELD OF THE INVENTION

The present invention relates generally to organic chemistry, analytical chemistry, biochemistry, molecular biology, genetics, diagnostics and medicine. In particular, it relates to fluorescence-based methods for genotyping diploid organisms.

BACKGROUND OF THE INVENTION

The following is offered as background information only and is not intended nor admitted to be prior art to the present invention.

The ability to detect DNA sequence variances in an organism's genome has become an important tool in the diagnosis of diseases and disorders and in the prediction of response to therapeutic regimes. It is becoming increasingly possible, using early variance detection, to diagnose and treat, even prevent the occurrence of, a disease or disorder before it has physically manifested itself. Furthermore, variance detection can be a valuable research tool in that it may lead to the discovery of genetic bases for disorders the cause of which were hitherto unknown or thought to be other than genetic.

The most common type of sequence variance is the single nucleotide polymorphism or SNP. As the name suggests, a SNP involves the substitution of one nucleotide for another at a particular locus in a gene. While each SNP involves a single nucleotide, a single gene may contain numerous SNPs.

It is estimated that SNPs occur in human DNA at a frequency of about 1 in 100 nucleotides when 50 to 100 individuals are compared. Nickerson, D. A., *Nature Genetics,* 1998, 223–240. This translates to as many as 30 million SNPs in the human genome. However, very few SNPs have any effect on the physical well-being of humans. Detecting the 30 million SNPs and then determining which of them are relevant to human health will clearly be a formidable task.

Complete DNA sequencing is presently the definitive procedure for accomplishing the above. However, current DNA sequencing technology is costly, time consuming and, in order to assure accuracy, highly redundant. Most sequencing projects require a 5- to 10-fold coverage of each nucleotide to achieve an acceptable error rate of 1 in 2,000 to 1 in 10,000 bases. In addition, DNA sequencing is an inefficient way to detect SNPs. While on the average a SNP occurs once in about every 100 nucleotides, when variance between two copies of a gene, for example those associated with two chromosomes, is being examined, a SNP may occur as infrequently as once in 1,000 or more bases. Thus, only a small segment of the gene in the vicinity of the SNP locus is really of interest. If full sequencing is employed, a tremendous number of nucleotides will have to be sequenced before any useful information is obtained. For example, to compare ten versions of a 3,000 nucleotide DNA sequence for the purpose of detecting four variances among them, even if only 2-fold redundancy is employed (each strand of the double-stranded 3,000 nucleotide DNA segment from each individual is sequenced once), 60,000 nucleotides would have to be sequenced (10×3,000×2). Furthermore, sequencing problems are often encountered that can require even more runs, often with new primers. Thus, as many as 100,000 nucleotides might have to be sequenced to detect four variances.

Determination of whether a particular gene of a species or of an individual of that species contains a SNP is called genotyping. Complete sequencing is, therefore, a method for accomplishing genotyping but, as is indicated above, it is slow, costly and extremely inefficient.

What is needed is a rapid, inexpensive, efficient, yet accurate, method for genotyping. The present invention provides such a method.

SUMMARY OF THE INVENTION

Thus, in one aspect, the present invention relates to a method for genotyping a diploid organism. A segment of each of the two alleles of a target gene of a diploid organism suspected to contain a polymorphism are obtained. The segments must include the suspected polymorphic locus from each allele. A first natural nucleotide suspected to be at the polymorphic locus is replaced at greater than 90% of its points occurrence in the first and the second segment with a first modified nucleotide to give a first and a second modified segment. A second natural nucleotide suspected to be at the polymorphic locus is replaced at greater than 90% of its points of occurrence in the first and the second modified segments with a second modified nucleotide to give a first and a second twice-modified segment. Replacement of the natural nucleotides with modified nucleotides comprises amplification using primers that hybridize to each segment or to each modified segment such that the suspected polymorphic locus is the first occurrence of a modified nucleotide after the 3' end of the primer in each amplified segment. The first and second twice-modified segments are then cleaved at greater than 90% of the points of occurrence of each modified nucleotide to give a first and second set of fragments, one fragment of each segment comprising primer and a modified nucleotide or residue thereof. At a selected point in the process a first fluorphore that emits light at a first wavelength is covalently bonded to at least a portion of the first modified nucleotides or residues and a second fluorophore that emits light at a second wavelength is covalently bonded to at least a portion of the second modified nucleotides or residues. The primer-containing fragments are isolated and analyzed spectroscopically for the emission of the first wavelength, the second wavelength, or both. If only one wavelength is detected, then the same modified nucleotide was incorporated at the suspected polymorphic locus in both allelic segments indicating that the alleles of the target gene are homozygous. If two wavelengths of light are detected, then a different modified nucleotide was incorporated at the suspected polymorphic locus in the allelic segment of the first and second alleles indicating that the alleles of the target gene are heterozygous.

In an aspect of this invention, isolating the primer-containing fragments comprises immobilizing the primer.

In an aspect of this invention, immobilizing the primer comprises hybridizing the primer to a complementary oligonucleotide that is bound to a solid support.

In an aspect of this invention, the primer is immobilized before amplification.

In an aspect of this invention, the primer is immobilized after amplification but before cleavage.

In an aspect of this invention, the primer is immobilized after cleavage.

In an aspect of this invention, isolating the primer-containing fragments comprises high performance liquid chromatography (HPLC).

In an aspect of this invention, isolating the primer-containing fragments comprises electrophoresis.

In an aspect of this invention, the fluorophores are covalently bonded to the first and second modified nucleotides prior to amplification.

In an aspect of this invention, the fluorophores are covalently bonded to a base moiety of the first, the second or both modified nucleotides.

In an aspect of this invention, cleavage comprises a reagent or reagents that cleave(s) at a 3' end of the modified nucleotide(s) having a fluorophore bonded to the base.

In an aspect of this invention, the first fluorophore is covalently bonded to the first modified nucleotide prior to amplification and the second fluorophore is bonded to a residue of the second modified nucleotide during cleavage.

In an aspect of this invention, bonding the second fluorophore to a residue of the second modified nucleotide during cleavage comprises cleaving the first and second twice-modified segments with a reagent comprising a chemical base and a fluorophore-containing phosphine. During cleavage, the residue of the second modified nucleotide forms a covalent bond with the fluorophore-containing phosphine.

In an aspect of this invention, the first fluorophore is covalently bonded to the first modified nucleotide after amplification but before cleavage and the second fluorophore is covalently bonded to a residue of the second modified nucleotide during cleavage.

In an aspect of this invention, the first fluorophore is covalently bonded to a residue of the first modified nucleotide after cleavage and the second fluorophore is bonded to a residue of the second modified nucleotide during cleavage.

In an aspect of this invention, bonding the first fluorophore to the first modified nucleotide comprises a functional group covalently bonded to the first modified nucleotide and another functional group covalently bonded to the fluorophore the two functional groups react with one another to form a bridge of covalently bonded atoms between the fluorophore and the modified nucleotide or modified nucleotide residue.

In an aspect of this invention, bonding the second fluorophore to the second modified nucleotide residue, comprises cleaving the modified nucleotide segments with a reagent comprising a base and a fluorophore-containing phosphine. During cleavage, the second modified nucleotide residue forms a covalent bond with the phosphine.

In an aspect of this invention, the phosphine comprises tris(2-carboxyethyl)-phosphine (TCEP) and the base is a secondary amine.

In an aspect of this invention, the TCEP comprises $N^1$-(5/6-carboxyfluorescein)-1,6-diaminohexane-TCEP.

In an aspect of this invention, the second modified nucleotide comprises 7-nitro-7-deazadeoxyadenine triphosphate, 7-nitro-7-deazadeoxyguanidine triphosphate, 5-hydroxydeoxycytidine triphosphate, 5-hydroxydeoxyuridine triphosphate or 5-aminodeoxyuridine triphosphate.

In an aspect of this invention, bonding the second fluorophore to a residue of the second modified nucleotide during cleavage comprises cleaving with a secondary amine that is covalently bonded to a fluorophore.

In an aspect of this invention, the first and second fluorophores are bonded, respectively, to at least 1% of the first and second modified nucleotides or residues thereof.

In an aspect of this invention, the first and second fluorophores are bonded, respectively, to at least 5% of the first and second modified nucleotides or residues thereof.

DETAILED DESCRIPTION OF THE INVENTION

Brief Description of the Tables

Table 1 is a chart of ten different PCR amplification reaction conditions used to examine the incorporation of two different modified nucleotides into a modified oligonucleotide.

Table 2 lists the temperature cycling protocol used in the above PCR amplifications.

BRIEF DESCRIPTION OF THE FIGURES

The figures herein are provided solely for the purpose of illustrating certain aspects of this invention. They are not intended, nor are they to be construed, to limit the scope of this invention in any manner whatsoever.

FIG. 7A shows the PCR amplification of a 48 base-pair and an 82 base-pair fragment of the transferrin receptor gene. The fragments amplified are shown with the primers underlined and the modified nucleotides bolded.

FIG. 7B shows the expected primer-containing fragments from the cleavage of the sequences shown in FIG. 7A.

DEFINITIONS

Figure 1:
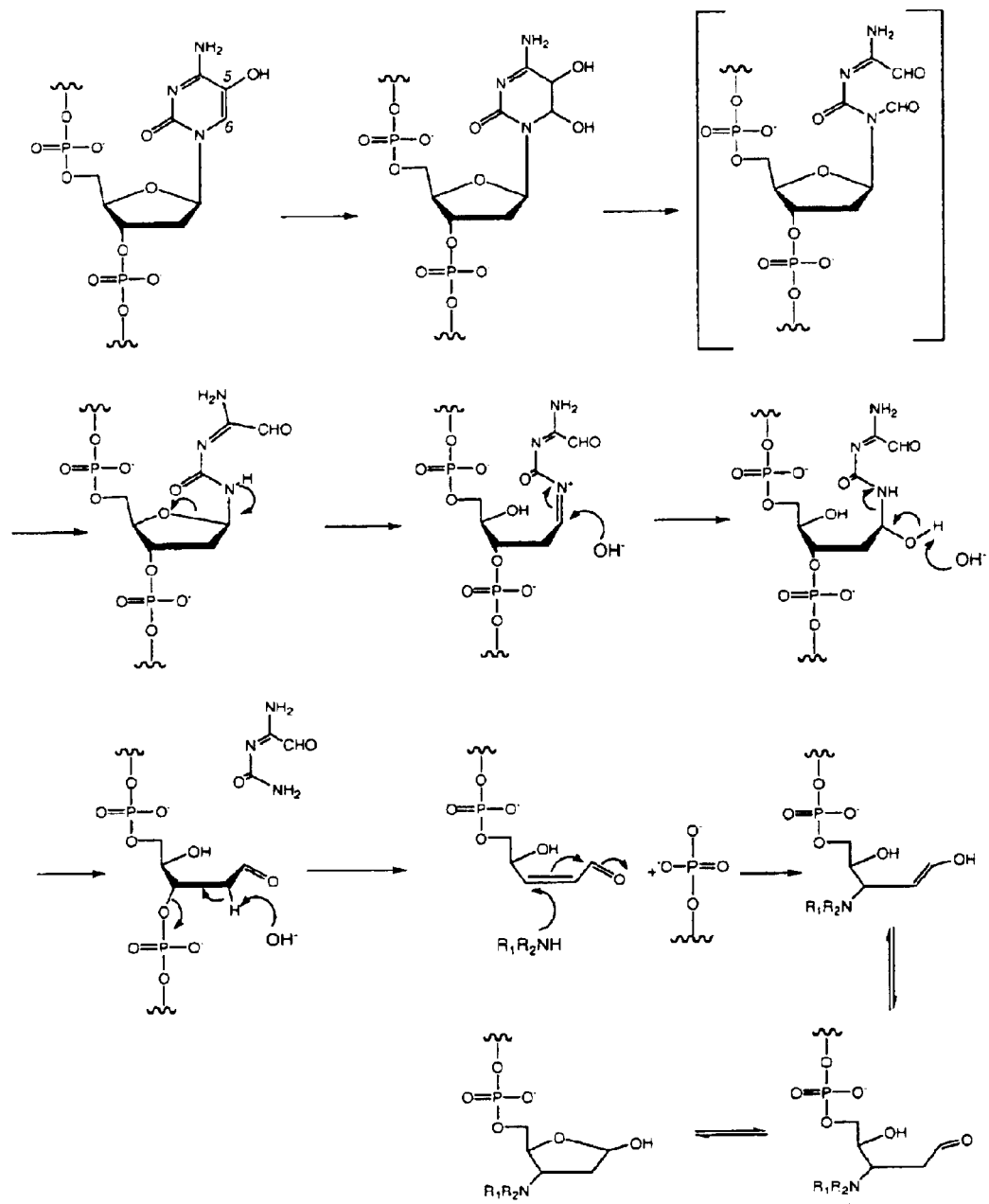
FIG. 1 shows the incorporation of a fluorophore into a nucleotide residue as the result of cleavage with a secondary amine. Either $R_1$ or $R_2$ may constitute the fluorophore.
Figure 2A:
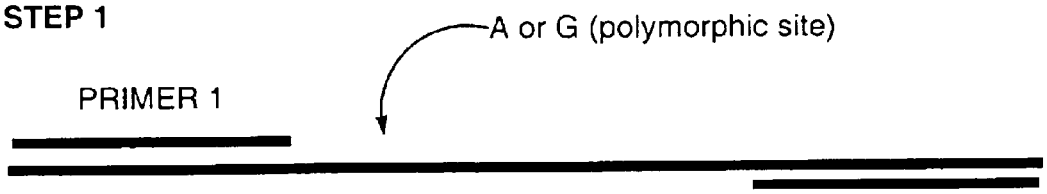
FIG. 2A shows method for preparation of fluorophore-containing cleavage fragments in which the fluorophores are bonded to the base of the modified nucleotides prior to amplification. Step 1 shows the primers and the polymorphic site, which for the purpose of this example, is an A/G polymorphism. Step 2 shows that, after chemical cleavage, two of the fragments formed contain the primer and a nucleotide residue containing the fluorophore. Step 3 shows an immobilized probe to which the primer can be hybridized to separate the primer-containing fragments for analysis.
Figure 2A:
Figure 2A:
Figure 2B:
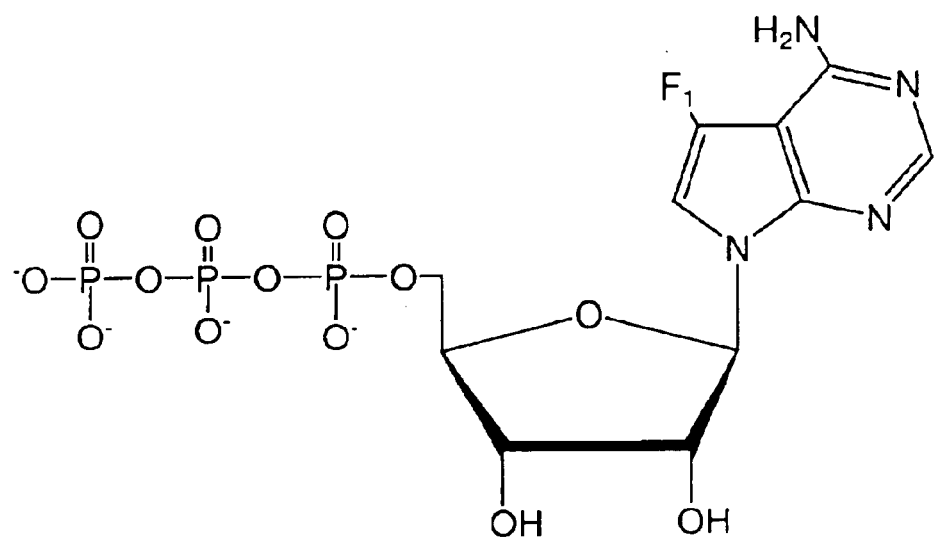
FIG. 2B shows the fluorophore-containing modified A and fluorophore-containing modified G used in the amplification described in FIG. 2A.
Figure 2B:
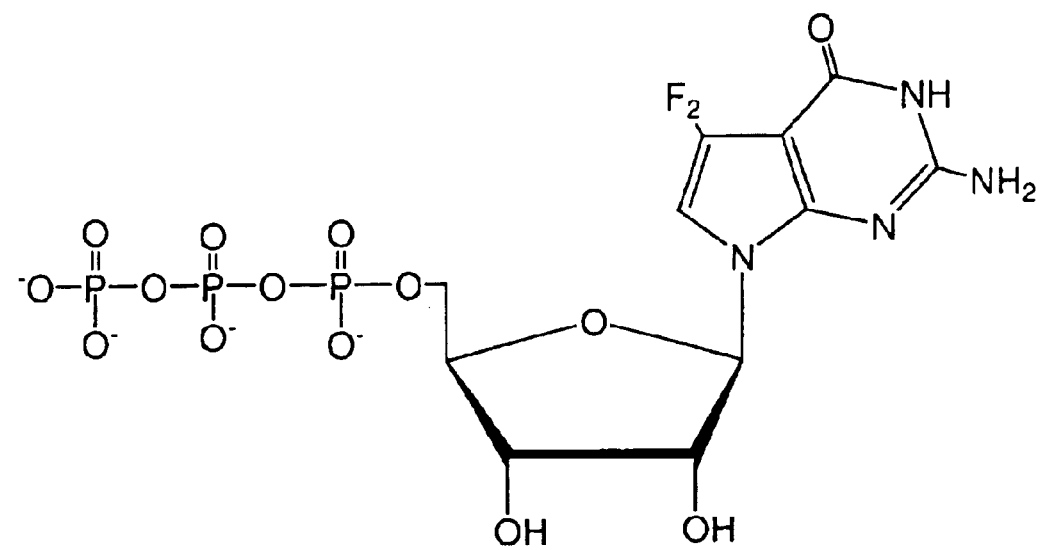

As used herein, a "gene" refers to the basic unit of heredity that carries the code for every physical trait that distinguishes an individual of a species.

As used herein, "genotyping" refers to the process of determining the single nucleotide polymorphisms (SNPs) present in the genes of a species or of an individual of that species.

As used herein, "diploid" refers to an organism in which each gene has two alleles, one on each chromosome of a homologous pair.

As used herein, an "organism" refers to any living entity comprised of eukaryotic cells. This includes plants, reptiles, fish, birds, animals and, in particular, human beings.

As used herein, an "allele" refers to an alternative form of a gene. More specifically, an allele is one of two or more different versions of a gene that can occupy the same position or locus on a chromosome. If the same allele occupies the position on both chromosomes of a diploid pair, that DNA, cell or individual is said to be "homozygous." In, on the other hand, the alleles occupying the same locus on the two chromosomes are different, the DNA, cell or individual is said to be "heterozygous."

As used herein, "isolating" the primer-containing fragments refers to separating them from the rests of the fragments, the cleavage reagents and any other materials that might have been carried along in the sequence of reactions that make up the methods herein. Isolating can be accomplished by any means that achieves the desired separation and any such means is within the scope of this invention. A presently preferred method for isolating the primer-containing fragments is immobilization of the fragments by hybridization of the primer to a substrate-bound complementary oligonucleotide. This can be accomplished prior to amplification, after amplification but before cleave, or after cleavage. Another presently preferred isolation technique is high performance liquid chromatography. A third presently preferred isolation procedure is electrophoresis, which includes, without limitation, gel electrophoresis and capillary electrophoresis.

As used herein, "analyzing" the primer-containing fragments refers to the spectrophotometric detection of the two different wavelengths of light emitted by the two fluorophores covalently bonded to the two modified nucleotide (or residues thereof) that correspond to the two natural nucleotides that can be at the suspected polymorphic locus. If only one of the wavelengths is detected, the alleles being examined are homozygous. If both wavelengths are detected, the alleles are heterozygous. Furthermore, the identity of the natural nucleotide at the suspected polymorphic site can be established since the first and second modified nucleotides carry fluorophores that emit at different wavelengths.

As used herein, a "reagent" refers to a chemical entity or physical force that cleaves a modified segment at the site of incorporation of a modified nucleotide. Such reagents include, without limitation, a chemical or combination of chemicals, normal or coherent (laser) visible or uv light, heat, high energy ion bombardment and irradiation. A "reagent" can refer to a single chemical entity or physical force, a combination of two or more chemical entities or physical forces or a combination of chemical entities and physical forces. If more than one chemical entity or physical force is used, they can be applied simultaneously or sequentially. By simultaneously is meant that two or more reagents are placed in the reaction mixture at the same time with a segment to be cleaved. It is understood that, once placed together in the reaction mixture, one of the reagents may in fact react with the segment before the other one. By sequentially is meant that a segment to be cleaved are first placed in contact with one reagent and only after that reagent has performed its function is the reaction product of the first reaction placed in contact with the second reagent, etc.

As used herein, a "single nucleotide polymorphism" or "SNP" refers to polynucleotide that differs from another polynucleotide at a particular locus by virtue of a single nucleotide exchange. A polynucleotide may, of course, contain numerous SNPs; however, each must occur at a different locus. For example, exchanging one A for one C, G or T at a particular locus in the sequence of a polynucleotide constitutes a SNP. When referring to SNPs, the polynucleotide is most often genetic DNA. SNPs can occur in coding and non-coding regions of the gene. Those in coding regions are of primary interest because it is they that can cause changes in the phenotype, i.e., an detectable physical difference in an individual compared to the general population. Detectable physical differences include, without limitation, a difference in susceptibility to a particular disease or disorder or a difference in response to a therapeutic regime used to treat or prevent a disease or disorder.

As used herein, a "polymorphic locus" refers to a location in the nucleotide sequence of the alleles of a gene of a diploid organism that may be occupied by different nucleotides. The difference may be the result of a SNP, a point mutation, a nucleotide insertion or a nucleotide deletion.

As used herein, a "suspected" polymorphic locus refers to a site in the alleles of a gene where a polymorphism is generally known to occur but it is unknown if the alleles of that gene in the single specific organism being examined contain the polymorphism.

As used herein, "amplifying" or "amplification" refers to the process of producing multiple copies of a segment of a double stranded polynucleotide by hybridizing natural nucleotide primers 5' to the segment to be amplified and then using a polymerase or polymerases to extend the primer to reproduce the sequences of the strands. A common amplification technique is PCR, the well-known polymerase chain reaction, which results in a logarithmic increase in the number of copies of the segment being amplified. The end result of amplification is the production of a sufficient amount of the segments to permit relatively facile manipulation. Manipulation refers to both physical and chemical manipulation, that is, the ability to move bulk quantities of the segments around and to conduct chemical reactions with them that result in detectable products.

As used herein a "segment" of an allele refers to a portion of the complete nucleotide sequence of the allele.

As used herein a "modified segment" refers to a segment in which a natural nucleotide has been replaced at greater than 90%, preferably greater than 95%, most preferably greater than 99% of its points of occurrence in the segment with a modified nucleotide. For the purposes of this disclosure, the phrase "at substantially each point of occurrence" will be used as a short-hand for the preceding list of preferences.

As used herein, a "twice-modified segment" refers to a modified segment in which a second, different natural nucleotide has been replaced at substantially each point of occurrence in the segment with a second, different modified nucleotide.

As used herein, to "include" a suspected polymorphic locus means that the SNP site is contained in the nucleotide sequence of the amplified twice-modified segment.

By "homozygous" is meant that the two alleles of a diploid cell or organism have exactly the same nucleotide sequence.

By "heterozygous" is meant that the two alleles of a diploid cell or organism have a difference in their nucleotide sequence at a particular locus. In most cases, the difference is a SNP, although it may be a mutation, an insertion or a deletion.

A "sequence" or "nucleotide sequence" refers to the order of nucleotide residues in a nucleic acid.

A "nucleoside" refers to a base covalently bonded to a sugar moiety. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA).

A "nucleoside triphosphate" refers to a nucleoside linked to a triphosphate group($O^-$—P(=O)($O^-$)—O—P(=O)($O^-$)—O—P(=O)($O^-$)—O-nucleoside). The triphosphate group has four formal negative charges that require counter-ions, i.e., positively charged ions. Any positively charged ion can be used, e.g., without limitation, $Na^+$, $K^+$, $NH_4^+$, $Mg^{2+}$, $Ca^{2+}$, etc. $Mg^{2+}$ is one of the most commonly used counter-ions. It is accepted convention in the art to omit the counter-ion, which is understood to be present, when displaying nucleoside triphosphates; the convention is followed in this application.

As used herein, unless expressly noted otherwise, the term "nucleoside triphosphate" or reference to any specific nucleoside triphosphate; e.g., adenosine triphosphate, guanosine triphosphate, cytidine triphosphate or thymidine triphosphate, refers to the triphosphate made using either a ribonucleoside or a 2'-deoxyribonucleoside.

A "nucleotide" refers to a nucleoside linked to a single phosphate group.

A "natural nucleotide" refers to an A, C, G or U nucleotide when referring to RNA and to dA, dC, dG and dT (the "d" referring to the fact that the sugar is deoxyribose) when referring to DNA. A natural nucleotide also refers to a nucleotide which may have a different structure from the above, but which is naturally incorporated into a polynucleotide sequence by the organism which is the source of the polynucleotide.

As used herein, a "modified nucleotide" refers to a nucleotide that meets two criteria. First, a modified nucleotide is a "non-natural" nucleotide. In one aspect, a "non-natural" nucleotide may be a natural nucleotide that is placed in non-natural surroundings. For example, in a polynucleotide that is naturally composed of deoxyribonucleotides, i.e., DNA, a ribonucleotide would constitute a "non-natural" nucleotide. Similarly, in a polynucleotide that is naturally composed of ribonucleotides, i.e., RNA, a deoxyribonucleotide would constitute a non-natural nucleotide. A "non-natural" nucleotide also refers to a natural nucleotide that has been chemically altered. For example, without limitation, one or more substituent groups may be added to the base, sugar or phosphate moieties of the nucleotide. Or, one or more substituents may be deleted from the base, sugar or phosphate moiety. Finally, one or more atoms or substituents may be substituted for one or more other atoms or substituents in the nucleotide. A "modified" nucleotide may also be a molecule that resembles a natural nucleotide little, if at all, but is nevertheless capable of being incorporated by a polymerase into a polynucleotide in place of a natural nucleotide.

The second criterion associated with a "modified" nucleotide, as the term is used herein, is that it alters the cleavage properties of the polynucleotide into which it is incorporated. For example, without limitation, incorporation of a ribonucleotide into a polynucleotide composed predominantly of deoxyribonucleotides imparts a heightened susceptibility to alkaline cleavage at the site of incorporation that does not otherwise exist. This second criterion of a "modified" nucleotide may be met by a single non-natural nucleotide substitution (e.g., the substitution of a ribonucleotide for a deoxyribonucleotide described above).

As used herein, "having different cleavage characteristics" refers to two or more modified nucleotides that, when incorporated into a polynucleotide, can be selectively cleaved in each other's presence by using different reagents and/or reaction conditions.

"Replacing" a natural nucleotide with a modified nucleotide refers to the process of amplifying a segment using one modified nucleotide and the three remaining natural nucleotides such that the natural nucleotide corresponding to the modified nucleotide is replaced at substantially each point of occurrence in the segment by the modified nucleotide.

"Cleaving" a twice-modified segment refers to the process of contacting the segment with a reagent that selectively severs the nucleotide chain at substantially each point of occurrence of a modified nucleotide.

As used herein, a "residue" of a modified nucleotide refers to whatever portion of the nucleotide remains attached to the primer-containing fragment after cleavage. For example, without limitation, in one aspect of this invention, the base moiety of a modified nucleotide is lost during cleavage with concurrent formation of a covalent bond between a phosphine and the sugar portion of the modified nucleotide that remains attached to the primer. This last entity would constitute the "residue" of the modified nucleotide.

A "polynucleotide" refers to a linear chain of 30 or more nucleoside monophosphate residues linked by phosphodiester bonds between the 3' hydroxyl group of one sugar and the 5' hydroxyl group of the next.

A "modified polynucleotide" refers to a polynucleotide in which a natural nucleotide has been replaced at substantially each point of its occurrence with a modified nucleotide. It may also refer to the replacement of two, three or four natural nucleotides with two, three or four modified nucleotides where each of the modified nucleotides alters the cleavage properties of the resulting modified polynucleotide differently. Cleavage can then be selectively carried out with each modified nucleotide in the presence of the others.

As used herein, to "alter the cleavage properties" of a polynucleotide means to render the polynucleotide more or less susceptible to cleavage at the point of incorporation of a modified nucleotide than it would be with a natural nucleotide or a different non-natural nucleotide at the same locus. It is presently preferred to "alter the cleavage properties" by rendering a polynucleotide more susceptible to cleavage at the site of incorporation of a modified nucleotide than at any other locus in the molecule. As used herein, the use of the singular when referring to nucleotide substitution or cleavage is to be construed as including substitution or cleavage at substantially each point of occurrence of a modified nucleotide unless expressly stated otherwise.

As used herein, a "template" refers to a polynucleotide strand, which a polymerase uses as a means of recognizing which nucleotide it should next incorporate into a growing strand to duplicate a polynucleotide. If the polynucleotide is DNA, it may be single-stranded or double-stranded. When employing the polymerase chain reaction (PCR) to amplify a template using the methods of this invention, the copies made may contain modified nucleotides. The modified segments are still capable of serving as templates for the production of further copies of identically modified amplicons.

As used herein, a "primer" refers to an oligonucleotide formed from natural nucleotides, the sequence of which is complementary to a segment of a template to be replicated. A polymerase uses the primer as the starting point for the replication process. By "complementary" is meant that the nucleotide sequence of a primer is such that it will hybridize to the template by formation of hydrogen bonded base-pairs over a length of at least ten consecutive bases. In the methods of this invention, a primer is never modified by replacement of a natural nucleotide with a modified nucleotide nor does cleavage ever occur in the nucleotide sequence of the primer.

As used herein, a "polymerase" refers, without limitation, to DNA or RNA polymerases, mutant versions thereof and to reverse transcriptases. DNA or RNA polymerases can be mutagenized by, without limitation, nucleotide addition, nucleotide deletion, one or more point mutations, "DNA shuffling" or joining portions of different polymerases to make chimeric polymerases. Combinations of these mutagenizing techniques may also be used. A polymerase catalyzes the assembly of nucleotides to form polynucleotides. Polymerases may be used either to extend a primer once or repetitively. Repetitive extension is sometimes referred to as amplification. Amplification may be accomplished by, without limitation, PCR, NASBR, SDA (Strand Displacement Amplification), 3SR (Self-Sustained Sequence Replication Reaction), TSA (Tyramide Signal Amplification) and rolling circle replication. In the methods of this invention, one or more polymerases and one or more extension or amplification techniques may be used to replicate a particular polynucleotide.

As used herein, a "chemical oxidant" refers to a reagent capable of increasing the oxidation state of a group on a molecule. For instance, without limitation, a hydroxyl group (—OH) can be oxidized to an aldehyde, ketone or acid.

Some examples of chemical oxidants are, without limitation, potassium permanganate, t-butyl hypochlorite, m-chloroperbenzoic acid, hydrogen peroxide, sodium hypochlorite, ozone, peracetic acid, potassium persulfate, and sodium hypobromite.

As used herein, a "chemical base" refers to a chemical compound that, in aqueous medium, has a pK greater than 7.0. A chemical base may be inorganic or organic. Examples of inorganic chemical bases include, without limitation, alkali (sodium, potassium, lithium) and alkaline earth (calcium, magnesium, barium) hydroxides, carbonates, bicarbonates, phosphates and the like. Ammonium hydroxide is another inorganic chemical base. Nitrogen-containing organic compounds such as pyridine, aniline, quinoline, morpholine, piperidine and pyrrole are also chemical bases. Nitrogen-containing chemical bases may be primary (the nitrogen has two hydrogen atoms and one other substituent on it), secondary (the nitrogen has one hydrogen and two other substituents on it) or tertiary (the nitrogen has no hydrogen atoms on it). Chemical bases may be used as aqueous solutions, which may be mild (usually due to dilution) or strong (concentrated solutions). A chemical base also refers to a strong non-aqueous organic base; examples include, without limitation, sodium methoxide, sodium ethoxide and potassium t-butoxide.

Secondary amines are presently preferred chemical bases for use in the cleavage of modified nucleotides. Secondary amines useful in the methods of this invention include, without limitation, pyrrolidine, piperidine, 3-pyrrolidinol, 2-pyrrolidinemethanol, 3-pyrrolidinemethanol, 4-hydroxypiperidine, 4-(2-hydroxyethyl)piperidine, hexamethyleneimine, heptamethyleneimine, diethylamine, diproylamine, dibutylamine, proline, morpholine, piperizine, picolinic acid, piperazine-2-carboxylic acid, 4-piperidineethanol and isopecotic acid. A secondary amine useful in the methods herein may also be polymer bound, for example, without limitation, piperidine-4-carboxylic acid polymine resin (polystyrene). A secondary amine may be covalently bonded to a fluorophore. The labeled secondary amine may then be used to cleave a twice modified segment hereof as the result of which the residue of the modified nucleotide will become covalently bonded to the amine and thereby will be labeled with the fluorophore.

As used herein, the term "acid" refers to a substance that dissociates in water to produce one or more hydrogen ions. An acid may be inorganic or organic. It may be a strong acid, which generally infers highly concentrated, or mild, which generally infers dilute. It is, of course, understood that acids inherently have different strengths; e.g., sulfuric acid is much stronger than acetic acid. The proper choice of acid will be apparent to those skilled in the art from the disclosures herein. Preferably, the acids used in the methods of this invention are mild. Examples of mild inorganic acids are, without limitation, dilute hydrochloric acid, dilute sulfuric acid, dilute nitric acid, phosphoric acid and boric acid. Examples, without limitation, of mild organic acids are formic acid, acetic acid, benzoic acid, p-toluenesulfonic acid, trifluoracetic acid, naphthoic acid, uric acid and phenol.

As used herein, "bond," "bonding" or "bonded" refers, unless otherwise expressly stated, to covalent bonds between the entities which are the subject of the bonding.

As used herein, a "functional group" refers, without limitation, to an entity such as amino (—$NH_2$), hydroxyl (—OH), cyano (—C≡N), nitro ($NO_2$), carboxyl (—COOH), acid halide (C(O)X, wherein X is chloro or bromo), ester (—C(O)OR, R is methyl ethyl, etc.), formyl (—CHO), keto (—$CH_2$C(O)$CH_2$—), alkenyl (—C═C—), alkynyl (—C≡C—), halo (F, Cl, Br and I ) groups and the like, which are capable of reacting with other functional groups to form bridges of covalently bonded atoms linking together the entities to which the functional groups were initially bonded. For instance, an amino functional group can react with an acid halide functional group to form an amide (—C(O)$NH_2$). Likewise, a hydroxyl group can react with an acid halide to form an ester. Many such functional groups are known to those skilled in the art. The use of any of them in the methods herein to link modified nucleotides to fluorescent tags are within the scope of this invention.

"Hybridizing" or "hybridization" refers to the formation of A-T or C-G base pairs among a string of contiguous nucleotides in an oligonucleotide or polynucleotide (usually at least 10 to form a stable hybridization product). In the present case, the oligonucleotides are a primer and a template or a primer and an immobilization oligonucleotide. To hybridize, the primer and template or primer and oligonucleotide must be "complementary" in the region of base-pair formation. "Complementary" means that the locus of each A, C, G and T (or U, if the oligonucleotide or template comprises ribonucleotides) in the sequence of the hybridizing portion of the primer corresponds to a T, G, C or A, respectively, in the same locus of the sequence of the template or oligonucleotide.

"Immobilized," "immobilizing," or "immobilization" refers to the attachment of a primer of this invention to a solid support. The support holds the primer or fluorophore-containing primer/modified nucleotide or fluorophore-containing primer/modified-nucleotide-reside at a designated location while physical or chemical manipulations, such as washing to remove impurities and byproducts, can be performed without dislodging it. Examples of solid supports include, without limitation, polymeric beads, the walls of a tubular column coated with a substance that will bind the primer, a filter paper or a lab chip. A plethora of such supports and means for immobilizing nucleotide-containing molecules thereon are known in the art. It will become apparent to those skilled in the art which supports may be useful in the methods herein and how to use them based on the disclosures herein. All such supports and methods are within the scope of this invention.

As used herein, "forming a bridge of covalent bonded atoms" refers to the product of the reaction of a functional group on one molecule, herein a modified nucleotide or residue thereof, with a functional group on another molecule, here, a fluorophore. An example, without limitation, of such a bridge is the reaction product of an acid halide, $R^1$C(O)X, where $R^1$ is a modified nucleotide and X is chloro or bromo, with a methyleneamine, $R^2$—$CH_2NH_2$, where $R^2$ is a fluorophore. The product is an amide, $R^1$C(O)NH$CH_2R^2$. In this example, the bridge of covalently bonded atoms would be $R^1$—C—N—C—$R^2$. Of course, a very large number of such functional groups and their reaction products are known to those skilled in the art. They and the "bridge of covalently bonded atoms" that results from their reactions are within the scope of this invention.

As used herein, a "fluorophore" refers to a molecule that absorbs energy at one wavelength of radiation and subsequently emits energy at another, different wavelength. Any molecule that can absorb any manner of radiation and emit detectable radiation at a different wavelength would be a "fluorophore" for the purposes of this invention and therefor within its scope. However, presently preferred fluorophores are those that absorb light, in particular but without limitation, ultraviolet light, at one wavelength and emit light at a different wavelength. The fluorophore may be fluorescent or phosphorescent. A fluorescent fluorophore emits light only so long as the stimulus is present. On the other hand, a phosphorescent fluorophore continues to emit light for a perceptible period time after the stimulus has been removed.

As used herein, the terms "selective," "selectively," "substantially," "essentially," "uniformly" and the like, mean that the indicated event occurs to a particular degree. For example, the percent incorporation of a modified nucleotide herein is characterized as "substantially complete." As used herein, this means greater than 90%, preferably greater than 95% and, most preferably, greater than 99%. With regard to cleavage at a modified nucleotide, "selectively" means greater than 10 times, preferably greater than 25 times, most preferably greater than 100 times that of the natural nucleotide in the modified polynucleotide. The percent cleavage at a modified nucleotide is also referred to herein as being "substantially complete." This means greater than 90%, preferably greater than 95%, most preferably greater than 99% complete.

Discussion

The methods of this invention can be used to examine the genetic DNA of an individual displaying symptoms of a particular disease or disorder known or suspected to be genetically based. Comparison of the DNA of the individual with that of healthy members of the same population will confirm whether the individual is afflicted with a particular genetically-related disease or disorder. Conversely, the method can be used to study an individual displaying symptoms of a disease or disorder of unknown origin to determine if it might have a genetic component.

Of course, the methods herein are not limited to the examination of the genetic aspects of diseases and disorders of human beings. For example, without limitation, plants have genetic variations that affect such traits as disease resistance, temperature accommodation, drought resistance, product size, crop yield, flavor, etc. Animals likewise have genetic variations that affect size, fertility, growth rate, disease resistance, body composition and the like. Knowing which genetic variations are responsible for these and may other beneficial characteristics can have significant economic impact. The methods of this invention are equally applicable to investigations into these areas of genetic inquiry.

Particularly useful aspects of the methods described herein are ease of assay design, low cost of reagents and suitability of the cleavage products for fluorescent detection.

Nucleotide Modification and Cleavage

A modified nucleotide may contain a modified base, a modified sugar, a modified phosphate ester linkage or a combination of these. With regard to the present invention, the presently preferred modified nucleotide is either a base-modified nucleotide or a ribonucleotide.

Base-modified Nucleotides

Base-modified nucleotide refers to the chemical modification of the adenine, cytosine, guanine or thymine (or, in the case of RNA, uracil) moiety of a nucleotide. The resulting modified nucleotide is more susceptible to cleavage than the natural nucleotides in the polynucleotide. The following are examples, without limitation, of base modification. Other modifications of bases will become apparent to those skilled in the art based on the disclosures herein. Such base modifications are within the scope of this invention.

1. Adenine (1) can be replaced with 7-deaza-7-nitroadenine (2). 7-Deaza-7-nitroadenine is readily incorporated into polynucleotides by various polymerases. The 7-nitro group activates C-8 to attack by chemical base such as, without limitation, aqueous sodium hydroxide or aqueous piperidine, which results in strand scission. Verdine, et al., *JACS*, 1996, 118:6116–6120.

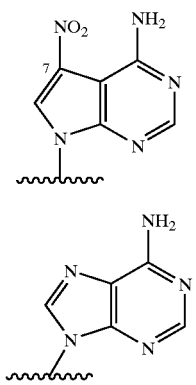

When the cleavage reaction is carried out in the presence of a phosphine, for example, without limitation, tris(2-carboxyethyl) phosphine (TCEP) and a base, complete cleavage is obtained. Thus, when DNA modified by incorporation of 7-nitro-7-deaza-2'-deoxyadenosine was treated with 0.2 M TCEP/1 M piperidine/0.5 M Tris base at 95° C. for one hour, complete cleavage was observed on denaturing polyacrylamide gel (20%) electrophoresis. Other bases such as, without limitation, ammonium hydroxide can be used in place of piperidine and Tris base. This procedure, i.e., the use of a phosphine in conjunction with a base, should work for any base-modified nucleotide in which the modified adenine, cytosine, guanine, thymine or uracil is labile to chemical base.

Secondary amines are presently preferred chemical bases for use in cleavage reactions of this invention. Some representative secondary amines useful in cleavage reactions of this invention include, without limitation, diethylamine, dipropylamine and pyrrolidine. However, secondary amines having a boiling point above 100° C. at atmospheric pressure are preferred. While not being bound to any particular theory, this might be due to the fact that lower boiling secondary amines are volatilized at the temperatures used for cleavage, 90° C. or higher, making it difficult to maintain an optimal concentration of the amine in the cleavage reaction. Examples of higher boiling secondary amines include, without limitation, dibutylamine, piperidine, 3-pyrrolidinol, hexamethyleneimine, morpholine and pyrazine. Secondary amines having a boiling point above 150° C. are even more preferable, with those having a boiling point above 200° C. being the presently most preferred. Such high boiling secondary amines include, without limitation, heptamethyleneimine, 3-pyrrolidinol, 2-pyrrolidinemethanol, 3-pyrrolidinemethanol, proline, picolinic acid, piperazine-2-carboxylic acid, 4-piperidineethanol, isonipecotic acid and piperidine-4-carboxlic acid polymine resin (polystyrene). 3-Pyrrolidinol, 2-pyrrolidinemethanol and 3-pyrrolidinemethanol piperidine-4-ethanol (4-(2-hydroxyethyl)piperidine) are presently preferred high boiling secondary amines for use in the methods of this invention.

When the cleavage reaction is carried out in the presence of a phosphine and a base, a unique adduct forms. For example, when the phosphine is tris(2-carboxyethyl) phosphine (TCEP), mass spectrometry of the product is consistent with a structure having a ribose-TCEP adduct at its 3' end and a phosphate moiety at its 5' end:

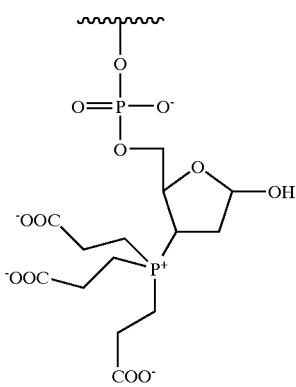

The mechanism of formation of the phosphine adduct is not presently known; however, without being held to any particular theory, the following is a possibility:

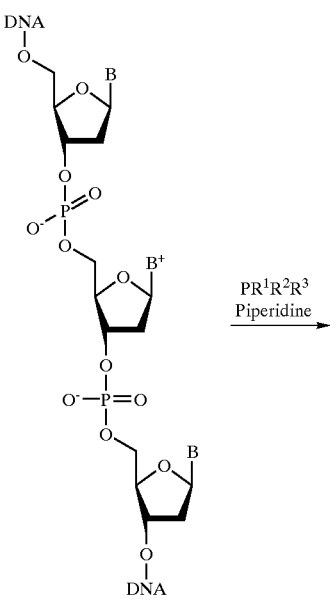

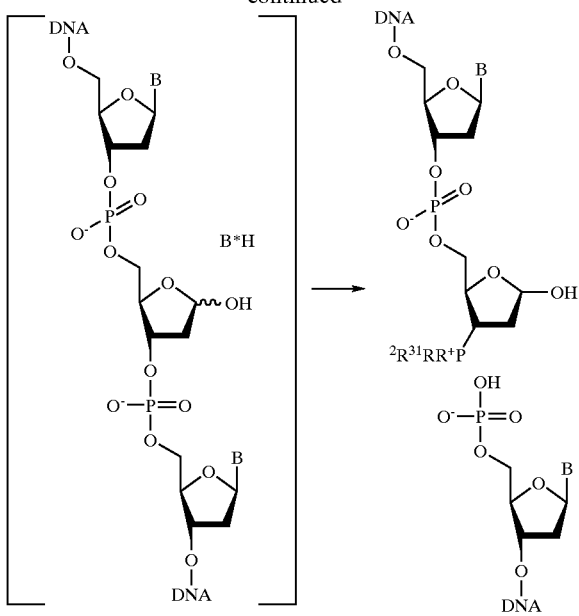

The incorporation of a phosphine into the cleavage product can be used to label polynucleotide fragments at the same time cleavage is being performed. By using a phosphine that contains a label or tag but is still capable of forming the above-described adduct, such entities as, without limitation, mass tags, fluorescence tags, radioactive tags and ion-trap tags can be incorporated directly into polynucleotide fragments during cleavage.

While other phosphines useful in the cleavage/tagging procedure described above will become apparent to those skilled in the art based on the disclosures herein, and therefore are within the scope of this invention, TCEP is presently preferred. The carboxy (—C(O)OH) groups of TCEP can be readily modified, for example, without limitation, by reaction with an amine, alcohol or mercaptan to form an amide, ester or mercaptoester:

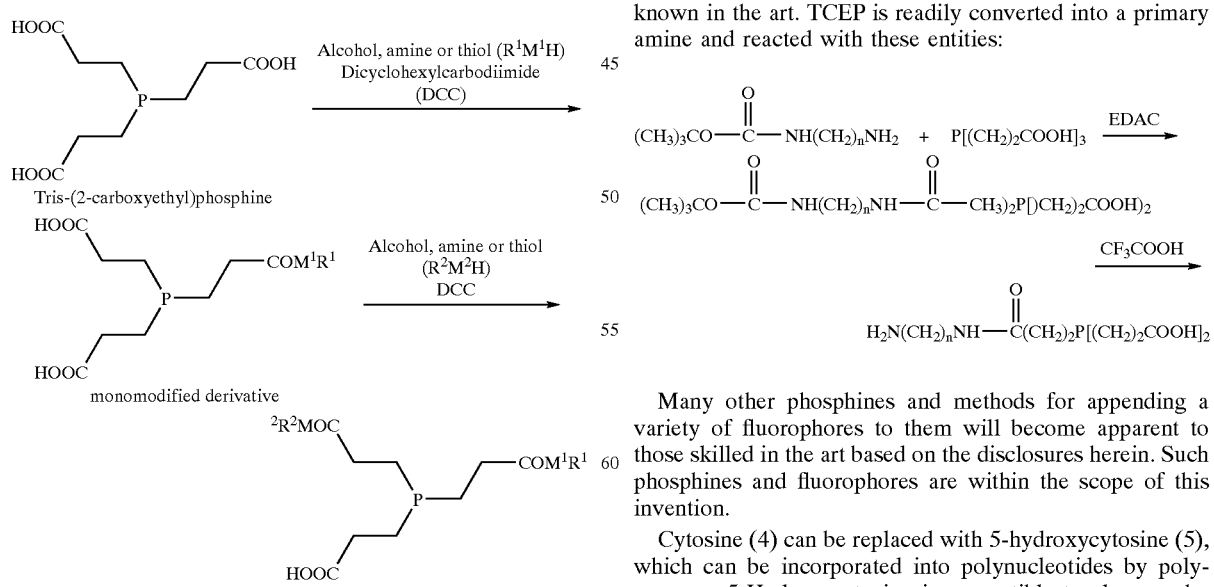

In the above scheme, $M^1$ and $M^2$ are independently oxygen, —NH, $NR^1$ or sulfur. $R^1$ and $R^2$ are independently mass, fluorescent, radioactive or ion trap tags.

When a carboxy group is reacted with a carbodiimide in the absence of a nucleophile, the product rearranges to form an N-acylurea. If the carbodiimide contains a fluorophore, the phosphine will then carry it:

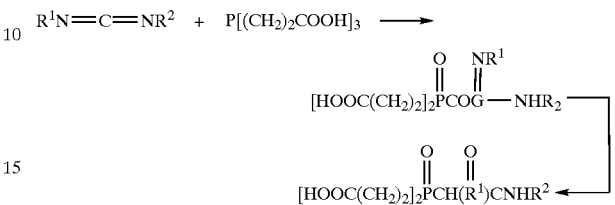

Amino group-containing fluorophores such as fluoresceinyl glycine amide, (5-aminoacetamido)fluorescein, 7-amino-4-methylcoumarin, 2-aminoacridone, 5-aminofluorescein, 1-pyrenemethylamine and 5-aminoeosin may also be used to prepare labeled phosphines. Amino derivatives of Lucifer Yellow and Cascade Blue can also be employed as can amino derivatives of biotin. In addition, hydrazine derivatives such as rhodamine and Texas Red hydrazine may be useful in this method.

Fluorescent diazoalkanes, such as, without limitation, 1-pyrenyldiazomethane, may be used to form esters with TCEP. Fluorescent alkyl halides may also react with the carboxylate anion (—C(O)O⁻) of the phosphine to form esters. Such halides include, without limitation, panacyl bromide, 3-bromoacetyl-7-diethylaminocoumarin, 6-bromoacetyl-2-diethylaminonaphthalene, 5-bromomethylfluorescein, BODIPY® 493/503 methyl bromide, monobromobimanes and iodoacetamides such as coumarin iodoacetamide. Naphthalimide sulfonate ester reacts rapidly with the anions of carboxylic acids in acetonitrile to give adducts which are detectable by absorption at 259 nm down to 100 femtomoles and by fluorescence at 394 nm down to four femtomoles.

There are also many amine-reactive fluorescent probes known in the art. TCEP is readily converted into a primary amine and reacted with these entities:

Many other phosphines and methods for appending a variety of fluorophores to them will become apparent to those skilled in the art based on the disclosures herein. Such phosphines and fluorophores are within the scope of this invention.

Cytosine (4) can be replaced with 5-hydroxycytosine (5), which can be incorporated into polynucleotides by polymerases. 5-Hydroxycytosine is susceptible to cleavage by chemical base, particularly aqueous base such as aqueous piperidine or aqueous sodium hydroxide.

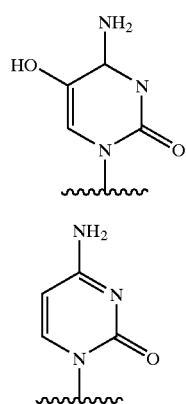

4

5

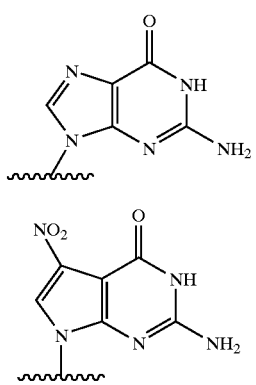

6

7

3. Guanine (6) can be replaced with 7-deaza-7-nitroguanine (7), which can be readily incorporated into polynucleotides by polymerases. The resulting nucleotide is susceptible to attack by chemical base, such as, without limitation, aqueous piperidine.

4. Either thymine (9) or uracil (10) may be replaced with 5-hydroxyuracil (11) (Verdine, *JACS*, 1991, 113:5104) or 5-aminouracil (12). As with the above-modified bases, these nucleotides can be incorporated into a polynucleotide by enzyme-catalyzed polymerization. While not absolutely necessary, in a presently preferred embodiment, cleavage of 5-hydroxyuracil is accomplished by first treating it with an oxidizing agent, for instance, aqueous permanganate, and then with a chemical base such as aqueous piperidine, as shown.

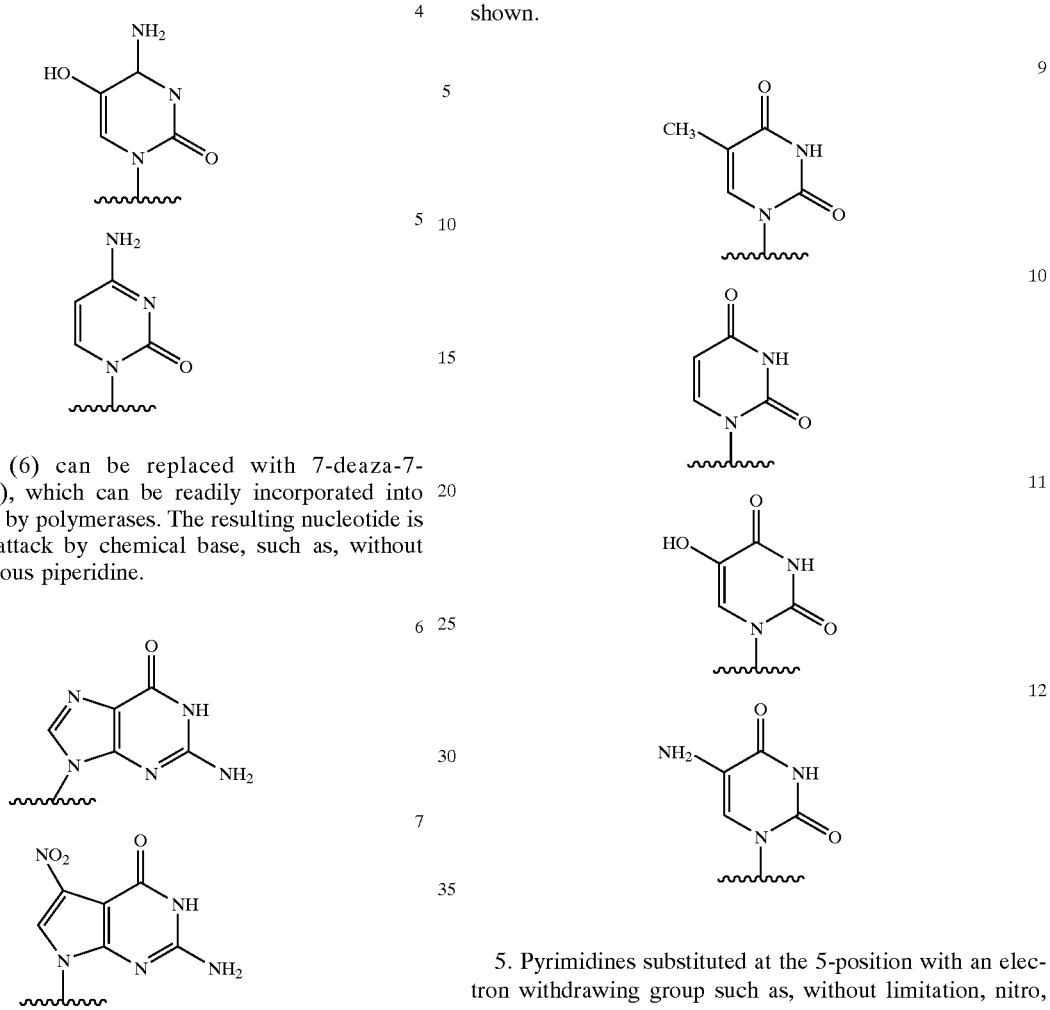

9

10

11

12

5. Pyrimidines substituted at the 5-position with an electron withdrawing group such as, without limitation, nitro, halo or cyano, should be susceptible to nucleophilic attack at the 6-position followed by base-catalyzed ring opening and subsequent degradation of the phosphate linkage. An example, which is not to be construed as limiting the scope of this invention in any manner, using 5-substituted cytidine is shown below. If the cleavage is carried out in the presence of tris(carboxyethyl)phosphine (TCEP), adduct 13 may be obtained. The TCEP may be functionalized with a fluorophore as discussed above.

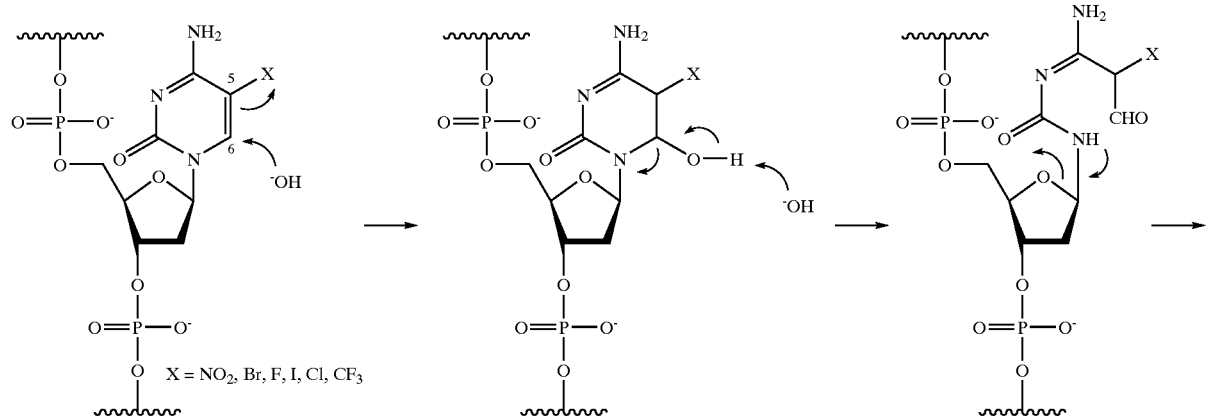

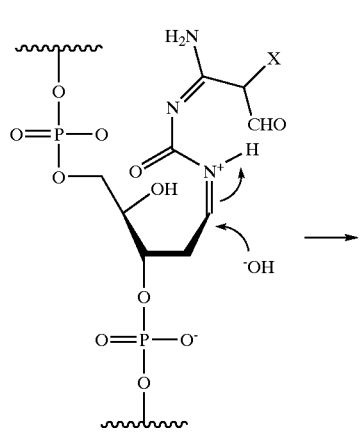
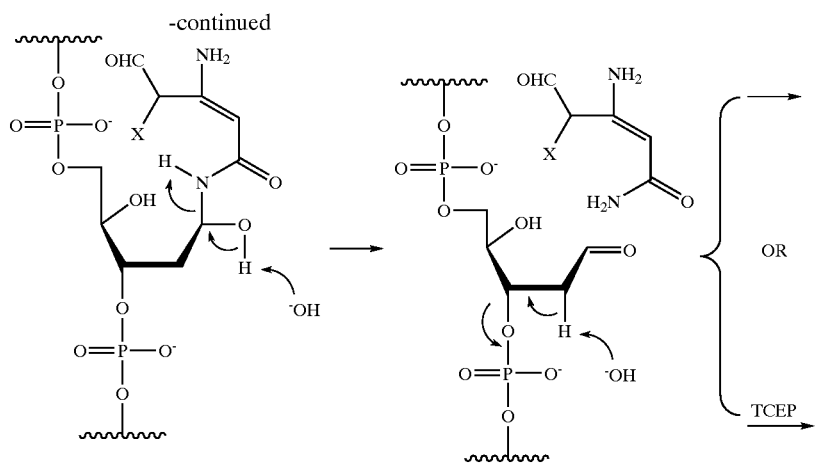
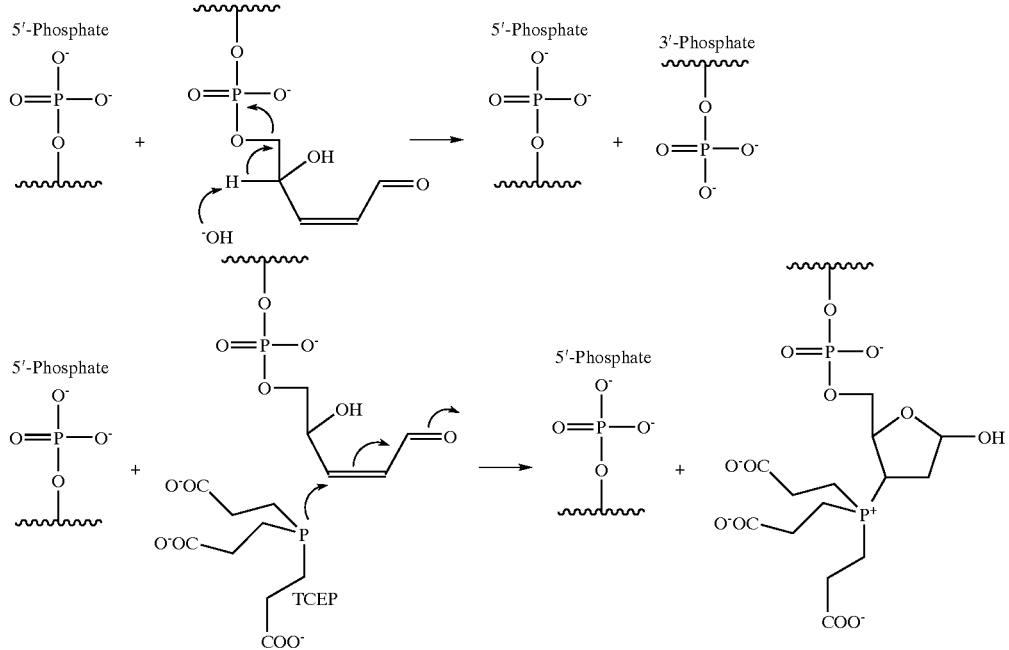

13

Secondary amines such as, without limitation, piperidine, pyrrolidine, morpholine, diethylamine may be also be used for labeling fragments during cleavage. In FIG. 1, DNA cleavage and fluorescence labeling using a secondary amine is shown. That $R_1$ or $R_2$ contains a fluorophore. It is emphasized that the reaction scheme shown in FIG. 1 represents a possible mechanism leading to one possible amine adduct and thus is not intended, nor is it to be construed as, limiting the scope of this invention in any manner whatsoever.

Oxidation with potassium permanganate, results in a labile intermediate that reacts with the amine to form a stable secondary amine-DNA adduct. The secondary amine can be functionalized with a fluorophore in the same manner as the primary amine phosphine derivative discussed above.

Genotyping

As DNA sequence data accumulates for various species, particularly humans, more and more variances in the genetic code for individuals compared to the general population within a species are being recognized. Some of these variances are being related to phenotypic differences such as an increased susceptibility to a particular disease or a different reaction to a given therapeutic regime. Thus, there is increasing demand for automated, accurate, high throughput, inexpensive methods for determining the status of a specific nucleotide or nucleotides in individuals where variation has been discovered. This procedure—the determination of the nucleotide at a particular location in a DNA sequence—is referred to as genotyping. The methods of this invention are eminently suitable to genotyping. First, a segment of DNA in which a SNP is known to occur in some individuals is replicated to produce enough of the segment with which to work. This can be accomplished by primer extension or by amplification. Amplification using PCR is presently preferred. The amplification is performed in the presence of two natural nucleotides and two base-modified nucleotides. The PCR primers are designed so that one of them is sufficiently near the polymorphic locus so that, during amplification, no modified nucleotide will be incorporated between the end of the primer and the polymorphic locus. That is, a base-modified nucleotide corresponding to the nucleotide suspected to be involved in the SNP will be the first cleavable site in the amplified segments. For example, if an A/T polymorphism is being genotyped, the modified nucleotides used will be modified A and modified T and the modified A or modified T will be the first modified nucleotide after the end of the primer.

When amplification is complete, the PCR reaction mixture is subjected to chemical cleavage, which severs the segments at the site of incorporation of each modified nucleotide. Since, by design, no modified nucleotide was incorporated between one of the primers and the polymorphic locus, among the fragments will be two that comprise the primer and a fragment of the segment containing the modified nucleotide(s) or a residue thereof at the polymorphic locus.

The two modified nucleotides or nucleotide residues representing the two potential allelic nucleotides that remain attached to the primer are substituted with two fluorophores that fluoresce at different wavelengths. While any percentage of the modified nucleotides or nucleotide residues of the methods herein may be labeled with fluorophore, and all such percentages are within the scope of this invention, only about 1% of them need to be so labeled. It is presently preferred, however, that at least 5% of the modified nucleotides or nucleotide residues be substituted with a fluorophore. Either or both of the fluorophores can be attached to the modified nucleotides before the amplification step, so long as the fluorophore does not interfere with the process. Or, one of the fluorophores can be placed on one of the modified nucleotides during cleavage using the above-discussed phosphine cleavage reaction. It is also possible to put the fluorophores on one or both modified nucleotides after cleavage by having a functional group on the modified nucleotide that will react with a functional group on the fluorophore. Different pairs of complementary functional groups can be used on the modified nucleotides and fluorophores. That is, one of the modified nucleotides can be substituted with a functional group that will react with the functional group on one of the fluorophores only. Likewise, the functional group on the other modified nucleotide is selected so that it only reacts with the functional group on the other fluorophore. It is also possible to use the same functional groups on the modified nucleotides and fluorophores by protecting one set of functional groups with blocking groups that prevent the functional groups from reacting until the blocking groups are removed.

Figure 3:
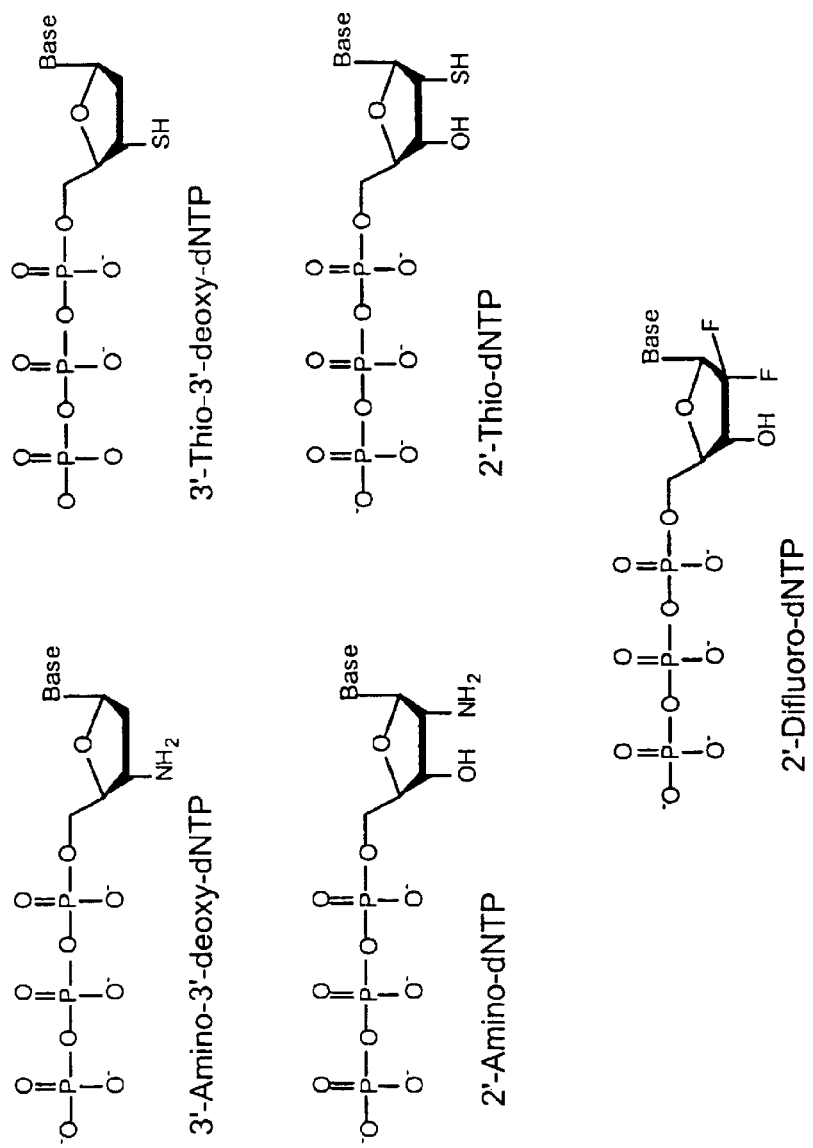
FIG. 3 shows some examples of 2'-deoxyribonucleotides analogs that cleave under acidic or basic conditions at the 3' position leaving the base intact. These nucleotides would thus be useful in the method illustrated in FIG. 2, wherein the fluorophore is bonded to the base.

An example of fluorophores bonded to the bases of modified nucleotides is shown in FIG. 2. There, two ribonucleotides corresponding to the polymorphic nucleotides, A and G, for example, are covalently bonded to fluorophores F1 and F2 (FIG. 2B). They are then used in a PCR reaction to amplify the target sequence. An immobilized probe is then used to bind the fragments containing either the A modified with fluorescent probe F1 or G modified with fluorescent probe F2. The probes have distinct signals and thus may be specifically detected and the particular allele identified (FIG. 2A). Many such fluorophore/ribonucleotides are commercially available, for instance from NEN (Boston, Mass.). Others could be created from such compounds as 3'-thio-3'-deoxy-, 3'-amino, 3'-deoxy-, z'-thio-, z'-amino and z-difluoro-z'-deoxy-ribonucleotides (FIG. 3). Chemical cleavage occurs 3' to these modified nucleotides so that fluorescent groups are retained on the fragment attached to the primer.

Figure 4:
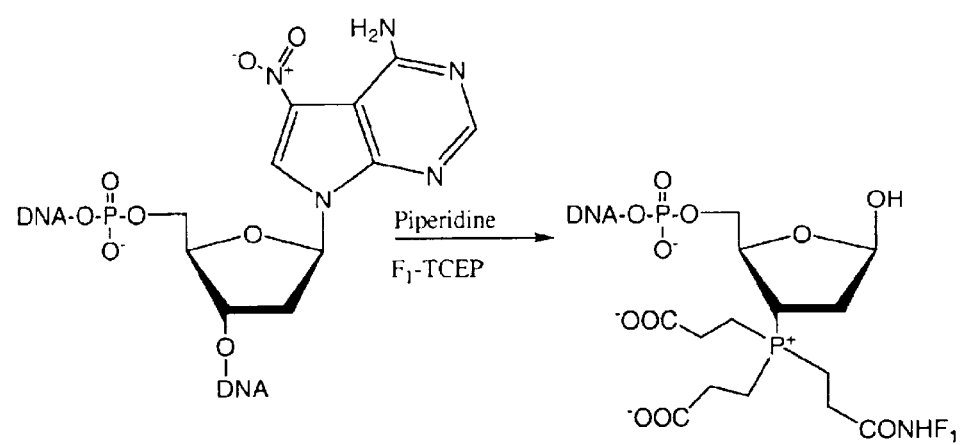
FIG. 4 shows a method for the preparation of fluorophore-containing cleavage fragments in which one of the fluorophores is bonded to one of the modified nucleotides prior to amplification while the other is substituted on a residue of the other modified nucleotide during cleavage. As can be seen in FIG. 4, chemical cleavage of the G allele occurs in normal fashion providing, as before, a fragment consisting of the primer and a fluorophore-containing residue. Chemical cleavage of the A allele, on the other hand, results in attachment of a fluorophore to a residue of the dA during the cleavage reaction by using an F1 modified reagent, as shown. The cleavage products are shown in FIG. 4. As above, the primer-containing fragments are hybridization to a complementary probe for further processing and analysis.
Figure 4:
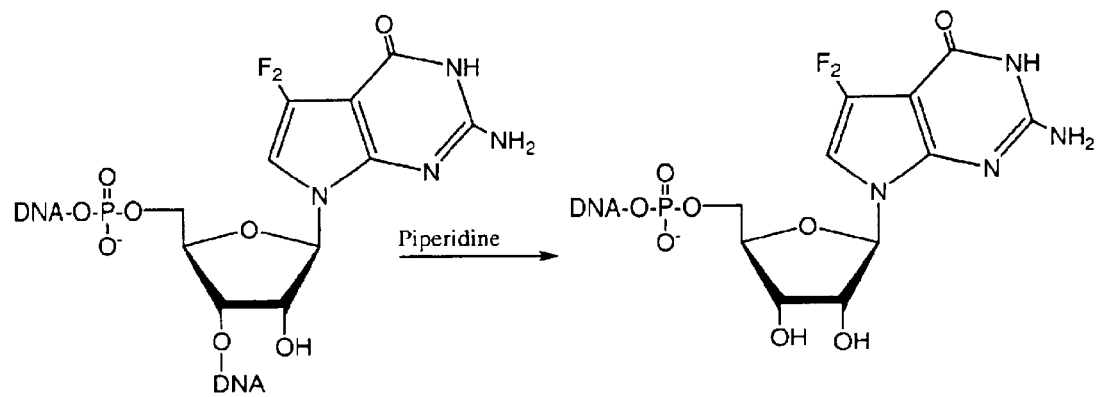

Another approach to labeling the modified nucleotides for use in the methods of this invention would be to label one modified nucleotide prior to amplification and the other during cleavage. This is exemplified in FIG. 4. There fluorophore F2 is attached to one of the modified nucleotides prior to amplification. Then, cleavage is performed using tris(carboxyethyl)phosphine, which has been substituted with a fluorophore. Under basic conditions, the modified G nucleotide carrying F2 is cleaved normally but [the] modified A nucleotide is cleaved with concomitant loss of the adenine base and formation of a covalent bond between the phosphine and the sugar portion of the residue. Modified nucleotides that will undergo this reaction include, without limitation, 7-nitro-deazadeoxyadenine, 7-nitro-7-deazadeoxyguanidine, 5-hydroxydeoxycytidine, 5-hydroxydeoxyuridine and 5-aminodeoxyuridine. Others will become apparent to those skilled on the art based on this disclosure and are within the scope of this invention.

Figure 5:
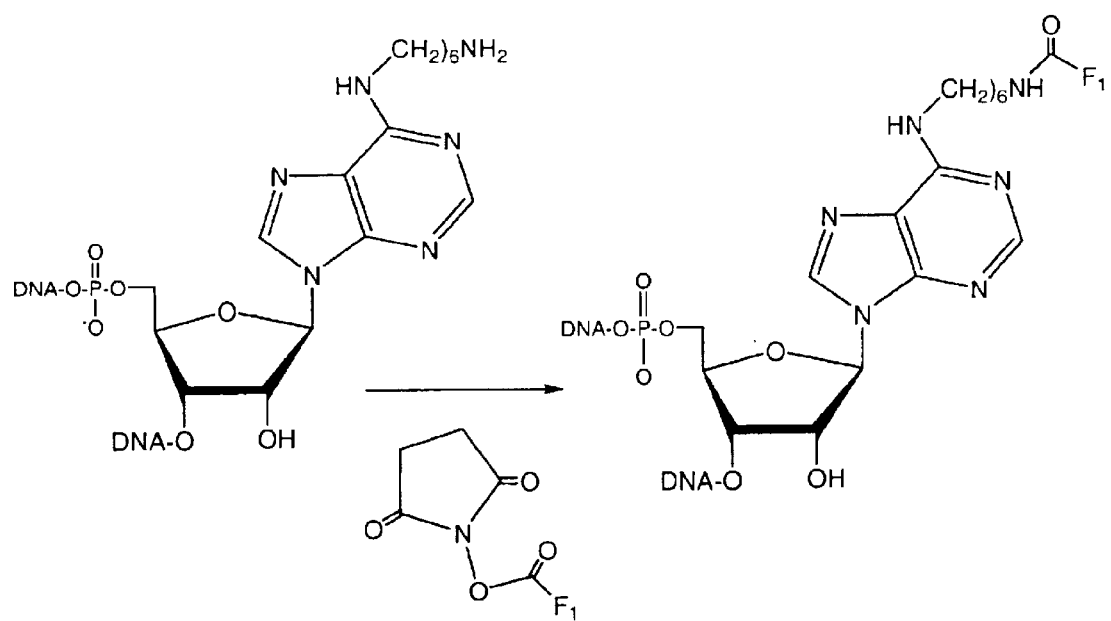
FIG. 5 shows a modified A nucleotide to which a fluorophore can be attached. This nucleotide can be used in a method for the preparation of fluorophore-containing cleavage fragments in which one of the fluorophores is attached to a residue of one of the modified nucleotides during cleavage (e.g., by the TCEP/piperidine cleavage approach) and one of the fluorophores is attached to the other modified nucleotide or a residue thereof at a convenient time after PCR amplification and before or after cleavage.

Another approach to labeling modified nucleotides with fluorophores is to have one of the modified nucleotides substituted with an entity that will react with a functional group on a fluorophore. This approach is shown in FIG. 5 wherein an adenine residue is shown substituted with a 6-aminohexyl group, which then, along with a 7-deaza-7-nitro-dGTP, is used to amplify the subject fragment (assuming it is either an A or G allele). The adenine allele can them be labeled by reaction with an appropriate fluorphore-containing entity such as that shown in FIG. 5. The modified G nucleotide is labeled with a second fluorophore that fluoresces at a different wavelength than the one used to label the A-allele using the base-phosphine cleavage reaction. Labeling the aminohexyl-containing base may precede or follow the base-phosphine cleavage reaction. In fact, when an amino- or thio- analog such as those shown in FIG. 3 are used instead of the $N^6$-(6-aminohexyl)-ATP depicted in FIG. 5, cleavage and labeling with F2 should be carried out first. In either case, two separate reactions are necessary to completely label the fragments, so it may be advantageous to immobilize the primer prior to cleavage/labeling to, among other things, simplify sample cleanup.

EXAMPLES

Example 1

Simultaneous Incorporation of Modified Nucleotides and Fluorescent Labeled Nucleotides in Amplified Segments The following example demonstrates the simultaneous incorporatation of both a modified nucleotide and a fluorescent modified nucleotide into a DNA segment during PCR amplification. It is also demonstrates cleavage of the PCR products following amplification at the modified nucleotides to give fluorescent labeled fragments.

Five reactions (Table 1, 1–5) were carried out using 7-nitro-7-deaza-dATP and five reactions (Table 1, 6–10) using 5-hydroxy dCTP. The volume for the components in each of the reactions are listed in Table 1 in microliters ($\mu L$). Some of the reagents were available commercially, namely, 10× PCR buffer (Gibco-BRL 11495-017 part no. 52395); 10× enhancer (Gibco-BRL 11495-017 part no. 52391); 1 mM fluorescein 12-dUTP (Molecular Probes, C-7604); and cloned Pfu polymerase 2.5 U/$\mu L$ (Stratagene 600159). Others were prepared by methods well-known in the art.

TABLE 1

| Reagents | \multicolumn{10}{c}{Reaction number} | | | | | | | | | |
|---|---|---|---|---|---|---|---|---|---|---|
| | 1 | 2 | 3 | 4 | 5 | 6 | 7 | 8 | 9 | 10 |
| 10X PCR Buffer | 2 | 2 | 2 | 2 | 2 | 2 | 2 | 2 | 2 | 2 |
| 10X Enhancer | 5 | 5 | 5 | 5 | 5 | 0 | 0 | 0 | 0 | 0 |
| 50 mM $MgSO_4$ | 0.8 | 0.8 | 0.8 | 0.8 | 0.8 | 0.8 | 0.8 | 0.8 | 0.8 | 0.8 |
| 20 M 2D6-4554-CF-NEW primer | 0.5 | 0.5 | 0.5 | 0.5 | 0.5 | 0.5 | 0.5 | 0.5 | 0.5 | 0.5 |
| 20 mM 2D6-4554-LR primer | 0.5 | 0.5 | 0.5 | 0.5 | 0.5 | 0.5 | 0.5 | 0.5 | 0.5 | 0.5 |
| 20 ng/mL Genomic DNA | 1 | 1 | 1 | 1 | 1 | 1 | 1 | 1 | 1 | 1 |
| 25 mM dGTP, dCTP, dTTP | 0.2 | 0.2 | 0.2 | 0.2 | 0.2 | 0.2 | 0.2 | 0.2 | 0.2 | 0.2 |
| 25 mM 7-nitro-7deaza-dATP | 0.2 | 0.2 | 0.2 | 0.2 | 0.2 | 0 | 0 | 0 | 0 | 0 |
| 25 mM 5-OH-dCTP | 0 | 0 | 0 | 0 | 0 | 0.2 | 0.2 | 0.2 | 0.2 | 0.2 |
| 1 mM Fluorescein 12-dUTP | 0 | 1.7 | 1 | 0.7 | 0.5 | 0 | 1.7 | 1 | 0.7 | 0.5 |
| Cloned pfu polymerase | 0.8 | 0.8 | 0.8 | 0.8 | 0.8 | 0.8 | 0.8 | 0.8 | 0.8 | 0.8 |
| Deionized water | 9 | 7.3 | 8 | 8.3 | 8.5 | 14 | 12.3 | 13 | 13.3 | 13.5 |

The ratio of fluorescein 12-dUTP to dTTP in reactions 2, 3, 4, and 5 above were approximately 1:3, 1:5, 1:7, and 1:10 respectively. The sequence amplified by PCR using the designated primers corresponds to bases 4533 to 4713 in the cytochrome P450 2D6 gene.

The reactions were cycled on a MWG Biotech Primus 96$^{Plus}$ thermocycler using the following protocol:

TABLE 2

| Step | Temperature | Time | No. of Cycles |
|---|---|---|---|
| 1 | 94° C. | 2 min | 1 cycle |
| 2 | 94° C. | 15 sec | Steps 2–4 |
| 3 | 55° C. | 15 sec. | 45 cycles |
| 4 | 72° C. | 2 min. | |
| 5 | 72° C. | 7 min | 1 cycle |
| 6 | 4° C. | indefinitely | hold |

Five µL of each sample were removed, mixed with loading buffer and separated by electrophoresis on a 2% agarose gel. The reaction number corresponds to the lane number. The gel was placed on a UV transilluminator and photographed using a Polaroid MP4 camera.

A green fluorescence could be detected in all the fragments containing fluorescein 12-dUTP but not in the control wells, which were amplified with modified nucleotides but without fluorescein 12-dUTP. Fluorescence observed in the control wells was orange, not green, indicating that it was due to trace amounts of ethidium bromide in the gel.

The agarose gel was stained with ethidium bromide and photographed to visualize the non-fluorescent labeled PCR fragments. Ethidium bromide staining resulted in observation of approximately the same intensities from all the PCR fragments regardless of whether they were amplified in the presence or absence of fluorescent nucleotides indicating that incorporation of the fluorescent nucleotide does not inhibit the PCR reaction.

The following reaction was carried out to determine whether a PCR reaction containing modified 5-hydroxy-dCTP and fluorescein 12-dUTP could be cleaved to form smaller labeled fragments. All the volumes are in µL.

| | | |
|---|---|---|
| A. | 10x PCRx buffer | 8 |
| B. | 50 mM $MgSO_4$ | 3.2 |
| C. | 20 uM 2D6-4554-CF-NEW primer | 2 |
| D. | 20 uM 2D6-4554-LR primer | 2 |
| E. | 20 ng/uL Genomic DNA | 4 |
| F. | 25 mM dATP, dGTP, dTTP | 0.8 |
| G. | 25 mM 5-OH-dCTP | 0.8 |
| H. | 1 mM Fluorescein-12-dUTP | 6.8 |
| I. | cloned Pfu polymerase 2.5 U/µL | 3.2 |
| J. | deionized water | 49.2 |

Figure 6:
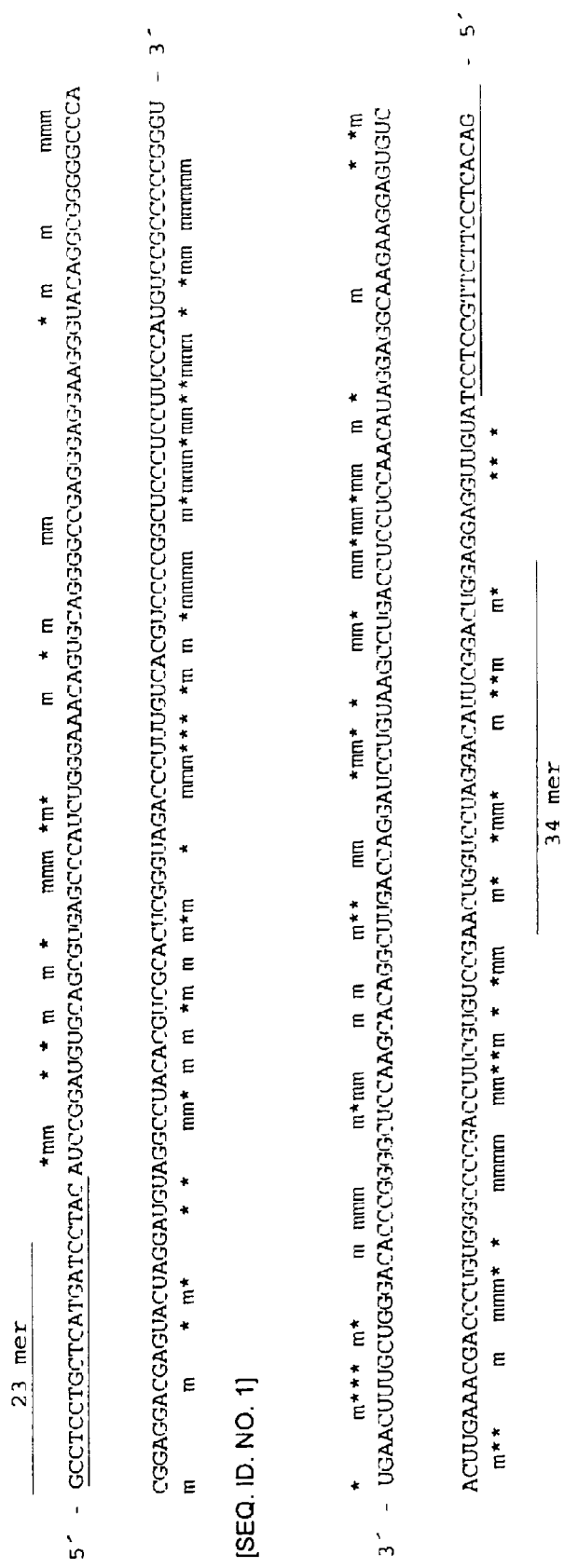
FIG. 6 shows a sequence that was amplified using 5-hydroxy-dCTP and fluorescein-12-dUTP as the modified nucleotides. The primer is underlined. The sites of incorporation of modified C have an "m" above the nucleotide and the sites of incorporation of modified U are shown with an asterisk (*) above the nucleotide.

The sequence amplified is shown below in FIG. 6. The primers are underlined. Modified nucleotides are indicated with an "m" above the nucleotide on the forward strand and below the nucleotide in the reverse strand. Fluorescein dU labeled nucleotides are identified by an asterisk ("*") above the nucleotide on the forward strand and below the nucleotide on the reverse strand. The sequence corresponds to a region of the cytochrome P450 2D6 gene from nucleotide 4533 to 4713.

The reactions were cycled on a MWG Biotech Primus 96$^{Plus}$ thermocycler using the protocol set forth in Table 2.

The reaction product was purified over a Sephadex G50 spin column to remove fluorescein 12-dUTP, which would interfere with the analysis. The following protocol was used for the purification:

A. re-suspend the resin in the Sephadex G50 spin column.

B. Remove the cap at the top and then the cap at the bottom of the Sephadex G50 spin column and let drain by gravity.

C. Spin the Sephadex G50 spin column in a Beckman TJ-6R centrifuge for 2 min. at 2000 rpm (1100×g).

D. Spin the Sephadex G50 spin column in a Beckman TJ-6R centrifuge one more time for 1 min. at 2000 rpm (1100×g) to remove the residual liquid in the tip.

E. Load the sample onto the Sephadex G50 spin column and spun in a Beckman TJ-6R centrifuge at 2000 rpm (1100× g) for 4 min.

The sample was dried in a Savant ISS 100 SpeedVac for 2 hours at high heat. The sample was then re-suspended in 16 µL of 10 mM Tris HCl pH 7.5. 1 µL of 10 mM $K_2MnO_4$ was added to the reaction, the sample was mixed by vortexing and centrifuged in an Eppendorf 5415C microcentrifuge for 5 seconds. The reaction was incubated for 5 minutes at room temperature. After incubation, 2.6 μL of 7.4 M pyrrolidine/38.5 mM EDTA was added to the tube, the sample was mixed by vortexing and centrifuged in an Eppendorf 5415C microcentrifuge for 5 seconds. The reactions were incubated at 94° C. for 1 hour in an MJ Research PTC100 thermocycler.

A 3 μL aliquot of the sample was mixed with 23 μL of loading dye containing Rox-labeled size standards of 10, 20, 30, 40 and 50 bases. 0.8 μL of sample with dye was loaded on a 15% Long Ranger acrylamide gel plate and electrophoresed on an ABI 377 sequencer. The run was analyzed using GeneScan analysis software. A chromatogram of the ABI 377 run showed the expected labeled 23mer and 34mer generated during chemical cleavage of the amplified PCR product.

Example 2

Incorporation of Two Modified Nucleotides by PCR/ fluorescent Labeling

Using a mixture of Taq polymerase (Promega) and a mutant Taq polymerase (Taq 346, Loeb, L. A., *J. Bio I. Chem.*, 2000, M008701200), a 48 bp or 82 bp fragment of the transferrin receptor gene (FIG. 7A) was amplified in the presence of 7-nitro-7-deaza-dATP/GTP/dCTP/TTP. As a control, the amplification was carried out using all natural nucleotides. To examine the cleavage properties of the amplicons, they were labeled with $^{32}$P at the 5' end and then treated with 1M pyrrolidine/0.25M TCEP/0.5M Tris/5 mM EDTA (1) or 1M piperidine/0.25M TCEP/0.5M Tris/5 mM EDTA (2) at 95° C. for one hour. The expected cleavage products are shown in FIG. 7B. The products obtained were analyzed by electrophoresis using 12% polyacrylamide gel. A autoradiogram confirmed that cleavage of modified G occurred at its 3' end to give a fragment in which the G base was retained. When treated with (1), cleavage at the 7-nitro-7-deaza-dA resulted in only one set of products resulting from removal of the modified nucleotide. When treated with (2), two sets of fragments were obtained, one of which was the TCEP adduct (indicated with a (+) sign in FIG. 7B). The difference in the cleavage reactions may be due to the fact that piperidine is less nucleophilic than pyrrolidine so that the TCEP can compete more effectively when the base is piperidine.

To demonstrate that a nucleotide already carrying a fluorophore could be used in a PCR reaction, an amplification reaction was carried out using dATP/GTP/fluorescein-12-GTP/dCTP/TTP. The expected PCR product was also observed by fluorescense-based polyacrylamide gel analysis on an ABI 377 instrument.

Example 3

A Fluorescein-labeled TCEP for Use in Cleavage/labeling of Modified Nucleotides

A. $N^1$-(5/6-carboxyfluorescein)-1,6-diaminohexane (2)

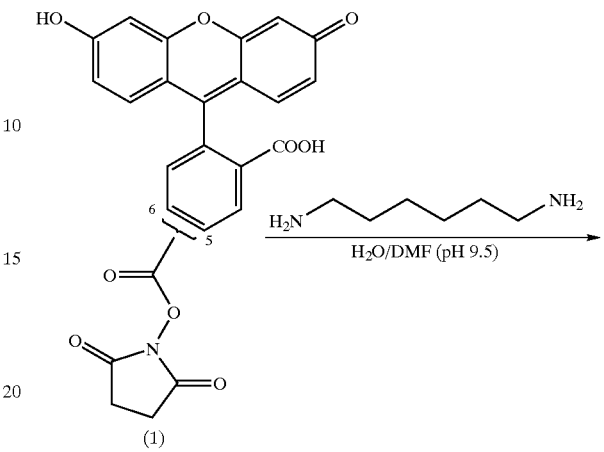

(1)

$C_{26}H_{19}NO_9$
Mol. Wt.: 489.43

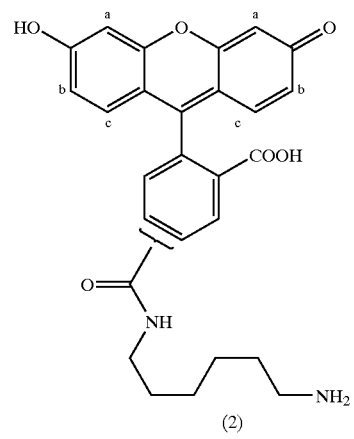

(2)

$C_{28}H_{30}N_2O_6$
Mol. Wt.: 490.55

5/6-Carboxyfluorescein (a mixture of approximately 60% 5-carboxy- and 40% 6-carboxy-fluorescein, Molecular Probes, Cat. No. C-1311, 90 mg, 0.1899 mmol) was dissolved in anhydrous N,N-dimethylformamide (4 mL). This solution was added dropwise with stirring to a 0.3 M aqueous solution (pH 9.5) of 1,6-diaminohexane. After stirring at room temperature for 2 hours, analysis by reverse-phase TLC. (C18-SiO$_2$), developed with 1:1 10 mM HCl:EtOH and visualized by long-wave UV, indicated two closely migrating compounds as the predominant fluorescent species. The reaction mixture was frozen on dry ice and then lyophilized to a voluminous orange solid. This material was re-dissolved in dH$_2$O, loaded onto a C18-SiO$_2$ reverse-phase chromatography column and eluted with 6:1 10 mM HCl:EtOH. The product containing fractions were pooled, frozen, and lyophilized to yield product as a bright orange solid (42.45 mg). $^1$H NMR (DMSO-d$_6$, 400 MHz): δ(ppm) 8.89 (0.6H, tr, amide NH of 5-isomer), 8.74 (0.4H, tr, amide NH of 6-isomer), 8.46 (0.6H, s, H4 of 5-isomer), 8.25 (0.6H, d, H6 of 5-isomer), 8.18 (0.4H, d, H4 of 6-isomer), 8.07 (0.4H, d, H5 of 6-isomer), 7.90 (3H, bs, NH$_3^+$), 7.67 (0.4H, s, H1 for 6-isomer), 7.38 (0.6H, d, H1 of 5-isomer), 6.72 (2H, m, FAM a), 6.57 (4H, m FAM b+c), 3.32 (1.2H, m, methylene 1 of 5-isomer), 3.19 (0.8H, m, methylene 1 of 6-isomer), 2.76 (2H, m, methylene 6), 1.56 (4H, m, ethylenes 2+5), 1.35 (4H, m, methylenes 3+4)

B. Fluorescein-diaminohexane-TCEP (FAM-C6-TCEP) (3)

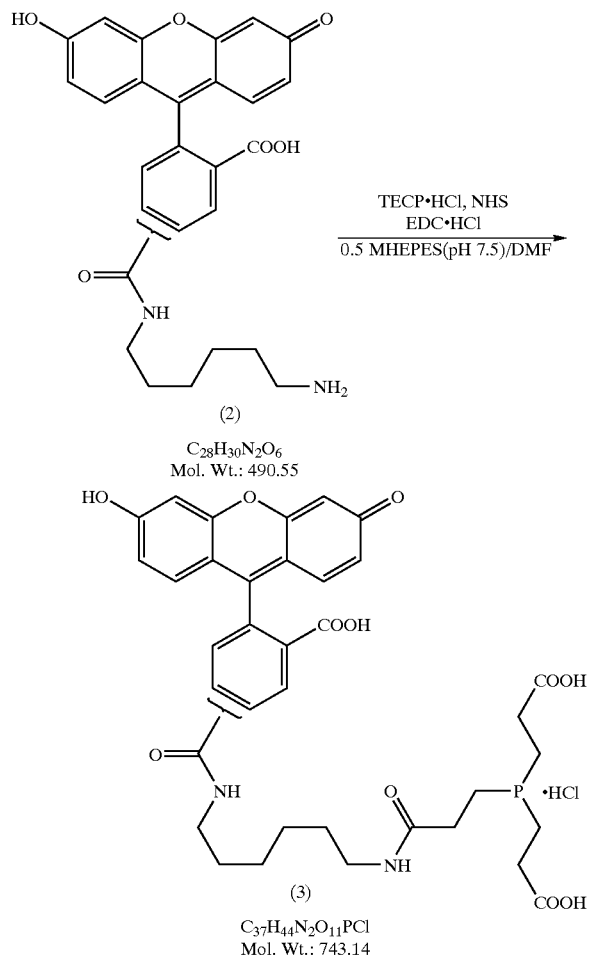

To a solution of tris-(2-carboxyethyl)phosphine hydrochloride (TCEP.HCl, 129 mg, 0.45 mmol) and N-hydroxysuccinimide (52 mg, 0.45 mmol) in 8 mL of 0.5 M HEPES (pH 7.5) and 4 mL N,N-dimethylformamide was added 1-(3-dimethylamino-propyl)-3-ethylcarbodiimide hydrochloride (86 mg, 0.45 mmol). Following 20 minutes of stirring at room temperature, $N^1$-(5/6-carboxyfluorescein)-1,6-diaminohexane (15 mg, 0.03 mmol) was added. After 80 minutes, the reaction mixture was acidified to pH 3 with conc. HCl. The mixture was frozen and lyophilized. The dried residue was re-dissolved in $dH_2O$, applied to a C18-SiO2 reverse phase chromatography column, and eluted with 6:1 10 mM HCl:EtOH. Product eluted as two fluorescent compounds with reverse-phase TLC mobilities that differed from that of the starting material (0.10–0.15 $R_f$ for products vs. 0.20–0.25 $R_f$ for starting material). The fractions containing these products were pooled, frozen, and lyophilized to yield a dark yellow residue (14.24 mg). $^1H$ NMR (DMSO-$d_6$, 400 MHz): δ(ppm) 8.95 (0.7H, tr, amide NH of 5-isomer), 8.78 (0.3H, tr, amide NH of 6-isomer), 8.47 (0.7H, s, H4 of 5-isomer), 8.27 (0.7H, d, H6 of 5-isomer), 8.20 (0.3H, d, H4 of 6-isomer), 8.08 (0.3H, d, H5 of 6-isomer), 8.00 (1H, m, NH), 7.70 (0.3H, s, H1 for 6-isomer), 7.37 (0.7H, d, H1 of 5-isomer), 6.72 (2H, m, FAM a), 6.57 (4H, m FAM b+c), 3.33 (1.4H, m, methylene 1 of 5-isomer), 3.20 (0.6H, m, methylene 1 of 6-isomer), 3.11 (2H, m, methylene 6), 2.42 (4H, m, TCEP methylenes), 2.28 (2H, m, TCEP methylenes), 1.99 (6H, m, TCEP methylenes), 2.76 (2H, m, methylene 6), 1.56 (2H, m, methylene 2 or 5), 1.45 (2H, m, methylene 5 or 2), 1.35 (4H, m, methylenes 3+4)

Although certain embodiments and examples have been used to describe the present invention, it will be apparent to those skilled in the art that changes in the embodiments and examples shown may be made without departing from the scope of this invention.

Other embodiments are contained within the following claims.

---

What is claimed:

1. A method for genotyping a diploid organism, comprising:

provinding two alleles of a target gene of a diploid organism suspected to contain a polymorphism;

obtaining a first segment of one allele wherein the segment includes the suspected polymorphic locus;

obtaining a second segment from the other allele wherein the segment also includes the suspected polymorphic locus;

replacing a first natural nucleotide, suspected to be at the polymorphic locus, at greater than 90% of its points of occurrence in the first and the second segment with a first modified nucleotide to give a first and a second modified segment;

replacing a second natural nucleotide, suspected to be at the polymorphic locus, at greater than 90% of its points of occurrence in the first and the second modified segments with a second modified nucleotide to give a first and a second twice-modified segment, wherein:

replacing the natural nucleotides with modified nucleotides comprises amplification using primers that hybridize to each segment or to each modified segment such that the suspected polymorphic locus will be the first occurrence of a modified nucleotide after the 3' end of the primer in each amplified segment;

covalently bonding a first fluorophore that emits light at a first wavelength to the first modified nucleotide or a residue thereof;

covalently bonding a second fluorophore that emits light at a second wavelength to the second modified nucleotide or a residue thereof;

cleaving the first and second twice-modified segments at greater than 90% of the points of occurrence of each modified nucleotide to give a first and second set of fragments, one fragment of each segment comprising primer and a modified nucleotide or residue thereof;

isolating the two primer-containing fragments;

analyzing the isolated fragments for the emission of the first wavelength of light, the second wavelength of light, or both, wherein:

if only one of the wavelengths is detected, then the same modified nucleotide was incorporated at the suspected polymorphic locus in both the first and the second allelic segments indicating that the alleles of the target gene are homozygous, whereas if both wavelengths are detected, then a different modified nucleotide was incorporated at the suspected polymorphic locus in the first and the second allelic segments indicating that the alleles of the target gene are heterozygous.

2. The method of claim 1, wherein isolating the primer-containing fragments comprises immobilizing the primer.

3. The method of claim 2, wherein immobilizing the primer comprises hybridizing the primer to a complementary oligonucleotide that is bound to a solid support.

4. The method of claim 3, wherein the primer is immobilized before amplification.

5. The method of claim 3, wherein the primer is immobilized after amplification but before cleavage.

6. The method of claim 3, wherein the primer is immobilized after cleavage.

7. The method of claim 1, wherein isolating the primer-containing fragments comprises high performance liquid chromatography (HPLC).

8. The method of claim 1, wherein isolating the primer-containing fragments comprises electrophoresis.

9. The method of claim 1, wherein the fluorophores are covalently bonded to the first and second modified nucleotides prior to amplification.

10. The method of claim 9, wherein the fluorophores are covalently bonded to a base moiety of the first, the second or both modified nucleotides.

11. The method of claim 10, wherein cleavage comprises a reagent or reagents that cleave(s) at a 3' end of the modified nucleotide(s) having a fluorophore bonded to the base.

12. The method of claim 1, wherein the first fluorophore is covalently bonded to the first modified nucleotide prior to amplification and the second fluorophore is bonded to a residue of the second modified nucleotide during cleavage.

13. The method of claim 12, wherein bonding the second fluorophore to a residue of the second modified nucleotide during cleavage, comprises:

cleaving the first and second twice modified segments with a reagent comprising a chemical base and a fluorophore-containing phosphine; wherein, the residue of the second modified nucleotide forms a covalent bond with the fluorophore-containing phosphine during cleavage.

14. The method of claim 13, wherein the phosphine comprises tris(2-carboxyethyl)phosphine (TCEP) and the chemical base is a secondary amine.

15. The method of claim 14, wherein the TCEP comprises $N^1$-(5/6-carboxyfluorescein)-1,6-diaminohexane-TCEP.

16. The method of claim 13, wherein the second modified nucleotide comprises 7-nitro-7-deazadeoxyadenine triphosphate, 7-nitro-7-deazadeoxyguanidine triphosphate, 5-hydroxydeoxycytidine triphosphate, 5-hydroxydeoxyuridine triphosphate or 5-aminodeoxyuridine triphosphate.

17. The method of claim 1, wherein the first fluorophore is covalently bonded to the first modified nucleotide after amplification but before cleavage and the second fluorophore is covalently bonded to a residue of the second modified nucleotide during cleavage.

18. The method of claim 1, wherein the first fluorophore is covalently bonded to a residue of the first modified nucleotide after cleavage and the second fluorophore is bonded to a residue of the second modified nucleotide during cleavage.

19. The method of either claim 17 or claim 18, wherein bonding the first fluorophore to the first modified nucleotide comprises:

a functional group covalently bonded to the first modified nucleotide; and, a functional group covalently bonded to the fluorophore that reacts with the functional group on the modified nucleotide to form a bridge of covalently bonded atoms between the fluorophore and the modified nucleotide or modified nucleotide residue.

20. The method of either claim 17 or claim 18, wherein bonding the second fluorophore to the second modified nucleotide residue, comprises:

cleaving the modified nucleotide segments with a reagent comprising a base and a fluorophore-containing phosphine; wherein, the second modified nucleotide residue forms a covalent bond with the phosphine during cleavage.

21. The method of claim 20, wherein the phosphine comprises tris(2-carboxyethyl)phosphine (TCEP) and the base is a secondary amine.

22. The method of claim 21, wherein the TCEP comprises $N^1$-(5/6-carboxyfluorescein)-1,6-diaminohexane-TCEP.

23. The method of claim 20, wherein the second modified nucleotide comprises 7-nitro-7-deazadeoxyadenine triphosphate, 7-nitro-7-deazadeoxyguanidine triphosphate, 5-hydroxydeoxycytidine triphosphate, 5-hydroxydeoxyuridine triphosphate or 5-aminodeoxyuridine triphosphate.

24. The method of any one of claim 12, 17 or 18, wherein bonding the second fluorophore to a residue of the second modified nucleotide during cleavage comprises cleaving with a secondary amine covalently bonded to a fluorophore.

25. The method of claim 1, wherein the fluorophores are bonded to at least 1% of each of the two modified nucleotide or nucleotide residues.

26. The method of claim 1, wherein the fluorophores are bonded to at least 5% of each of the two modified nucleotide or nucleotide residues.

* * * * *